US010077455B2

(12) United States Patent
Kildegaard et al.

(10) Patent No.: US 10,077,455 B2
(45) Date of Patent: Sep. 18, 2018

(54) 3HP TOLERANCE

(71) Applicant: TECHNICAL UNIVERSITY OF DENMARK, Kgs. Lyngby (DK)

(72) Inventors: Kanchana Rueksomtawin Kildegaard, Kgs. Lyngby (DK); Irina Borodina, Kgs. Lyngby (DK); Jochen Förster, Kgs. Lyngby (DK); Jens Nielsen, Kgs. Lyngby (DK)

(73) Assignee: TECHNICAL UNIVERSITY OF DENMARK, Kgs. Lyngby (DK)

( * ) Notice: Subject to any disclaimer, the term of this patent is extended or adjusted under 35 U.S.C. 154(b) by 149 days.

(21) Appl. No.: 14/896,905

(22) PCT Filed: Jun. 12, 2014

(86) PCT No.: PCT/EP2014/062267
§ 371 (c)(1),
(2) Date: Dec. 8, 2015

(87) PCT Pub. No.: WO2014/198841
PCT Pub. Date: Dec. 18, 2014

(65) Prior Publication Data
US 2016/0130613 A1    May 12, 2016

(30) Foreign Application Priority Data
Jun. 14, 2013  (EP) ..................... 13172151

(51) Int. Cl.
C12P 7/00       (2006.01)
C12P 7/42       (2006.01)
C12N 9/04       (2006.01)
C12P 7/52       (2006.01)

(52) U.S. Cl.
CPC .............. *C12P 7/42* (2013.01); *C12N 9/0006* (2013.01); *C12P 7/52* (2013.01); *C12Y 101/01284* (2013.01)

(58) Field of Classification Search
None
See application file for complete search history.

(56) References Cited

U.S. PATENT DOCUMENTS

| | | | |
|---|---|---|---|
| 7,700,319 B2 | 4/2010 | Liao et al. | |
| 7,785,837 B2 | 8/2010 | Liao et al. | |
| 8,883,464 B2* | 11/2014 | Lynch | A61L 15/24 |
| | | | 435/136 |
| 2007/0107080 A1 | 5/2007 | Liao et al. | |
| 2009/0081746 A1* | 3/2009 | Liao | C12N 15/52 |
| | | | 435/160 |
| 2010/0136638 A1 | 6/2010 | Liao et al. | |
| 2011/0244575 A1* | 10/2011 | Lipscomb | C12N 9/0008 |
| | | | 435/471 |

FOREIGN PATENT DOCUMENTS

| | | |
|---|---|---|
| EP | 2 505 656 | 10/2012 |
| WO | 01/16346 | 3/2001 |
| WO | 02/42418 | 5/2002 |
| WO | 2010/011874 | 1/2010 |
| WO | 2011/038364 | 3/2011 |
| WO | 2012/019175 | 2/2012 |
| WO | 2012/074818 | 6/2012 |

OTHER PUBLICATIONS

International Search Report dated Aug. 7 2014 in International Patent Application No. PCT/EP2014/062267.
Yasokawa, Daisuke et al., "Toxicogenomics using Yeast DNA Microarrays", Journal of Bioscience and Bioengineering, vol. 110, No. 5, available online Jul. 10, 2010, pp. 511-522.
Kumar, Vinod et al., "Recent advances in biological production of 3-hydroxypropionic acid", Biotechnology Advances, vol. 31, Nov. 1, 2013, pp. 945-961.
Erdeniz, Naz et al.,"Cloning-Free PCR-Based Allele Replacement Methods", Genome Research, vol. 7, downloaded from genome. cshlp.org on Mar. 11, 2016, pp. 1174-1183.
Gietz, R. Daniel et al., "Transformation of yeast by lithium acetate/ single-stranded carrier DNA/polyethylene glycol method", Methods in Enzymology, vol. 350, Feb. 2002, pp. 87-96.
Fernandez, M. Rosario et al., "A Double Residue Substitution in the Coenzyme-binding Site Accounts for the Different Kinetic Properties between Yeast and Human Formaldehyde Dehydrogenases", Journal of Biological Chemistry, vol. 274, Issue 53, downloaded from ://www.jbc.org/ on Feb. 26, 2016, pp. 37869-37875.
Grant, Chris M. et al., "Glutathione synthetase is dispensable for growth under both normal and oxidative stress conditions in the yeast *Saccharomyces cervisiae* due to an accumulation of the dipeptide gamma-glutamylcysteine", Molecular Biology of the Cell, vol. 8, Sep. 1997, pp. 1699-1707.
Hügler, Michael, et al., "Malonyl- Coenzyme A Reductase from Chloroflexus Aurantiacus, a Key Enzyme of the 3-Hydroxypropionate Cycle for Autotrophic C02 Fixation", Journal of Bacteriology, vol. 184, No. 9, May 2002, pp. 2404-2410.
Kwak, Suryang, et al., "Biosynthesis of 3-hydroxypropionic Acid from Glycerol in Recombinant *Escherichia coli* Expressing Lactobacillus brevis dhaB and dhaR Gene Clusters and *E. coli* K-12 aldH", Bioresource Technology, vol. 135, May 2013, pp. 432-439.
Luo, Lian Huo et al., "Production of 3-hydroxypropionic Acid Through Propionaldehyde Dehydrogenase PduP Mediated Biosynthetic Pathway in Klebsiella pneumoniae", Bioresource Technology, vol. 103, No. 1, Jan. 2012, pp. 1-6.
Molin, Mikael et al., "Dihydroxyacetone detoxification in *Saccharomyces cerevisiae* involves formaldehyde dissimilation", Molecular Microbiology, vol. 60, No. 4, Mar. 29, 2006, pp. 925-938.
Rathnasingh, Chelladurai et al., "Development and Evaluation of Efficient Recombinant *Escherichia coli* Strains for the Production of 3-hydroxypropionic Acid from Glycerol", Biotechnology and Bioengineering, vol. 104, No. 4, Nov. 2009, pp. 729-739.

(Continued)

*Primary Examiner* — Anand U Desai
(74) *Attorney, Agent, or Firm* — Pillsbury Winthrop Shaw Pittman LLP

(57) ABSTRACT

Cells and cell cultures are provided that have improved tolerance to 3-hydroxypropionic acid (3HP). Genetic modifications to provide a mutated or overexpressed SFA1 gene or other enhancement of 3HP detoxification via a glutathione-dependent dehydrogenase reaction, including medium supplementation with glutathione, may be combined with a 3HP producing metabolic pathway.

11 Claims, 7 Drawing Sheets

Specification includes a Sequence Listing.

(56) References Cited

OTHER PUBLICATIONS

Lian Hua Luo et al., "Stimulation of reductive glycerol metabolism by overexpression of an aldehyde dehydrogenase in a recombinant Klebsiella pneumoniae strain defective in the oxidative pathway," J. Ind. Microbiol. Biotechnol., vol. 38, pp. 991-999 (2011).

Shaohong Wen et al., "Utilization of amino acids to enhance glutathione production in *Saccharomyces cerevisiae*," Enzyme and Microbial Technology, vol. 35, pp. 501-507 (2004).

\* cited by examiner

3HP TOLERANCE

CROSS REFERENCE TO RELATED APPLICATIONS

This application is the National Phase entry of PCT/EP2014/062267, which claims priority to European Patent Application No. 13172151.6, filed Jun. 14, 2011 The content of these applications is incorporated herein by reference in their entirety.

FIELD OF THE INVENTION

The present invention relates to microbial cells, for instance cells of yeast strains, that show tolerance to 3-hydroxypropionic acid (3HP), including cells which produce 3HP.

BACKGROUND

3HP has been produced by metabolically engineered strains of *E. coli*, see for instance WO2011/038364, EP2505656 and WO02/42418 and increased tolerance to 3HP thereby produced has been sought. Production of 3HP in yeast has also been described, see WO2012/019175.

3HP is toxic to *S. cerevisiae* and this limits the ability to produce 3HP using a metabolically engineered *S. cerevisiae*. It would be desirable to produce yeasts generally and *S. cerevisiae* strains especially that are resistant to the toxic effects of 3HP so as to provide a starting point for further genetic modification to provide an operative metabolic pathway for the production of 3HP. It would also be desirable to provide yeasts which do produce 3HP and which have enhanced resistance to its toxicity. Such 3HP tolerant yeasts can provide the basis for industrial production of 3HP by cultivation of yeasts.

The SFA1 gene (alternatively named ADH5) of *Saccharomyces cerevisiae* in its wild type form has the gene sequence of SEQ ID NO:1. The gene is thought to encode an S-(hydroxymethyl)glutathione dehydrogenase.

It has been reported that Sfa1p is a member of the class III alcohol dehydrogenases (EC: 1.1.1.284), which are bifunctional enzymes containing both alcohol dehydrogenase and glutathione-dependent formaldehyde dehydrogenase activities. The glutathione-dependent formaldehyde dehydrogenase activity of Sfa1p is required for the detoxification of formaldehyde, and the alcohol dehydrogenase activity of Sfa1p can catalyze the final reactions in phenylalanine and tryptophan degradation. Sfa1p is also able to act as a hydroxymethylfurfural (HMF) reductase and catabolize HMF, a compound formed in the production of certain biofuels. Sfa1p has been localized to the cytoplasm and the mitochondria, and can act on a variety of substrates, including S-hydroxymethylglutathione, phenylacetaldehyde, indole acetaldehyde, octanol, 10-hydroxydecanoic acid, 12-hydroxydodecanoic acid, and S-nitrosoglutathione.

The five ethanol dehydrogenases (Adh1p, Adh2p, Adh3p, Adh4p, and Adh5p) as well as the bifunctional enzyme Sfa1p are also involved in the production of fusel alcohols during fermentation. Fusel alcohols are end products of amino acid catabolism (of valine, leucine, isoleucine, methionine, phenylalanine, tryptophan, and tyrosine) via the Ehrlich pathway and contribute to the flavour and aroma of yeast-fermented foods and beverages. They may also have physiological roles. For example, exposing cells to isoamyl alcohol, derived from catabolism of leucine, stimulates filamentous growth. Similarly, other fusel alcohols also stimulate filamentous growth in *S. cerevisiae* and biofilm formation in the pathogens *Candida albicans* and *Candida dubliniensis*.

Transcription of SFA1 is controlled by Sko1p, a negative regulator of the Hog1p transcription regulation pathway. SFA1 is induced in sko1 null mutants and in cells overproducing the transcription factor Yap1p. Sfa1p expression is also induced by chemicals such as formaldehyde, ethanol and methyl methanesulfonate. sfa1 null mutants are viable and display hypersensitivity to formaldehyde, whereas overproduction of Sfa1p results in increased resistance to formaldehyde.

Sfa1p displays similarity to Adh1p, Adh2p, Adh3p and Adh5p, and to the alcohol dehydrogenases of *Escherichia coli, Schizosaccharomyces pombe, Kluyveromyces marxianus, Kluyveromyces lactis, Candida albicans, Candida maltosa*, horse, rat, and mouse, as well as human ADH2 and ADH3, which are associated with the development of Parkinson disease. Sfa1p also exhibits similarity to the glutathione-dependent formaldehyde dehydrogenase of *Arabidopsis* (FALDH), which is able to complement the formaldehyde-hypersensitivity defects of sfa1 null mutants. Sfa1p is also similar to the glutathione-dependent formaldehyde dehydrogenases of mouse and human (ADH5), which are involved in the catabolism of S-nitrosoglutathione, a type of S-nitrosothiol central to signal transduction and host defence.

Formaldehyde is formed by oxidative demethylation reactions in many plants and methylotrophic organisms, but *Saccharomyces cerevisiae* is a non-methylotrophic yeast and cannot metabolize methanol to formaldehyde. However, *S. cerevisiae* is exposed to exogenous formaldehyde from plant material or in polluted air and water.

Concentrations of formaldehyde of 1 mM or higher are cytostatic or cytotoxic to haploid wild-type cells. Any free formaldehyde in vivo spontaneously reacts with glutathione to form S-hydroxymethylglutathione. The level of enzymes involved in the degradation of formaldehyde, such as Sfa1p and Yjl068Cp, determine the level of formaldehyde toxicity, and cells overproducing Sfa1p are resistant to formaldehyde and null mutants in either sfa1 or yjl068c are hypersensitive to formaldehyde. Sfa1p is induced in response to chemicals such as formaldehyde (FA), ethanol and methyl methanesulphonate, and Yjl068Cp is also induced in response to chemical stresses. Molin and Blomberg, Molecular Microbiology (2006) 60(4), 925-938 reported that SFA1 overexpression enhanced formaldehyde tolerance in *S. cerevisiae*. They reported also that supplementation of a culture medium with glutathione restored DHA sensitivity of a gsh1Δ strain.

Formate dehydrogenase is encoded by FDH1/YOR388C and FDH2. In some strain backgrounds of *S. cerevisiae*, FDH2 is encoded by a continuous open reading frame comprised of YPL275W and YPL276W. However, in the systematic sequence of S288C, FDH2 is represented by these two separate open reading frames due to an in frame stop codon.

It has been reported that the effect of certain mutations in SFA1 or SFA1 deletion has been to decrease resistance to formaldehyde, S-nitrosoglutathione, and peroxynitrite (Fernández, et al, 1999).

There would on this basis appear to be no known reason why certain mutations in SFA1, or its overexpression should be expected to improve 3HP tolerance.

We have found that a genetic modification providing overexpression of SFA1 or providing certain mutations of SFA1 increases the ability of yeast and other cells to grow in the presence of normally inhibitory concentrations of 3HP. Furthermore, we have found that supplementation of a culture medium with glutathione also enables cells to grow in a normally inhibitory concentration of 3HP.

Cells incorporating such a genetic modification form an improved platform for further genetic engineering to provide a 3HP expression pathway in the cells.

SUMMARY OF THE INVENTION

In a first aspect, the invention provides a cell having a metabolic pathway producing 3-hydroxypropionic acid (3HP), said cell exhibiting tolerance for 3HP and having one or more genetic modifications that provide for an enhanced activity of 3HP detoxification by a reaction pathway that includes a glutathione-dependent dehydrogenase reaction.

A said genetic modification conferring said tolerance may be one or more mutations in a gene encoding a glutathione-dependent formaldehyde dehydrogenase. Said one or more mutations may be in a gene equivalent to SFA1 of *Saccharomyces cerevisiae*, the gene sequence of which is seen in SEQ ID NO 1.

Thus, for instance, said one or more mutations may be in a gene encoding a protein having the sequence SEQ ID NO 1 or a protein with more than 80% homology to SEQ ID NO 1.

The term '3HP detoxification' as used herein includes any process by which a cell is enabled to tolerate the presence of 3-HP at a concentration that would otherwise be detrimental. It is thereby recognised that the toxic effects normally exhibited by 3-HP may be the consequence of 3-HP being transformed in vivo to a more directly toxic compound, and detoxification includes reducing the concentration of such a more toxic 3HP metabolite.

The reaction pathway may be one in which S-(3-hydroxypropanoyl_glutathione is converted to 3-HP.

Preferably, the mutation is at a position equivalent to the position aa276 Cys and/or at aa283 Met of the Sfa1p of *Saccharomyces cerevisiae*. Suitable specific mutations include Cys276→Ser, Cys276→Val, Cys276→Thr, Cys276→Gly, Cys276→Ala and/or Met283→Ile, Met283→Ala, Met283→Val. However, other amino acids may be substituted in these positions with like effect.

A said genetic modification may be such as to produce overexpression of a native, or heterologous, or mutated glutathione-dependent formaldehyde dehydrogenase to confer said 3HP tolerance.

Generally, a genetic mutation may be said to produce overexpression of a gene when the production of the gene product of the overexpressed gene is increased as compared to that of a parent organism (which may be termed 'wild type') which lacks said genetic modification but is otherwise the same as the overexpressing organism. Said increase may for instance be by 25% or more, 50% or more, 100% or more, or 200% or more. The genetic modification may involve the introduction of one or more further copies of a gene expressing the relevant gene product. The genetic modification may alternatively or additionally involve the use of a heterologous promoter or a more active endogenous promoter to control expression of a gene expressing the relevant gene product. Forced evolution or mutagenesis may be used to produce micro-organism strains which overexpress one or more native genes. All such methods may be applied to the overexpression of any gene product referred to herein.

Preferably, said genetic modification produces overexpression of a native or heterologous glutathione-dependent formaldehyde dehydrogenase which has the sequence SEQ ID NO 1 or is a protein with more than 80% homology to SEQ ID NO 1.

Additionally or alternatively, the cell is genetically modified for increased production of glutathione. To this end, it may be that the cell overexpresses the glutathione biosynthetic genes gamma-glutamylcysteine synthetase and glutathione synthetase. Additionally or alternatively, it may be that the cell overexpresses genes that enhance the production of amino acid precursors for glutathione biosynthesis.

3HP producing pathways may comprise several combinations of exogenous genes and overexpressed native genes. In general, 3HP can be obtained by utilizing pathways via at least four different intermediates: malonyl-CoA, glycerol, lactate, or beta-alanine (FIG. 1). Bacterial or fungal hosts can be used, where fungal hosts have an advantage of being able to tolerate low pH, therefore enabling a more economical process without the need for neutralization during fermentation and acidification on recovery.

Malonyl-CoA can be reduced to 3HP via combined action of malonyl-CoA reductase (malonate semialdehyde-forming) (E.C. 1.2.1.75) and 3-hydroxypropionate dehydrogenase (E.C. 1.1.1.59/E.C. 1.1.1.298) or 3-hydroxyisobutyrate dehydrogenase (E.C. 1.1.1.31) or by a bi-functional malonyl-CoA reductase (E.C. 1.2.1.75_1.1.1.298), for example from *Chloroflexus aurantiacus* (WO02/42418). Furthermore the host can be engineered for improved supply of precursor and redox co-factor as MCR requires NADPH (Hügler et al., 2002).

Glycerol conversion to 3HP via glycerol dehydratase (E.C. 4.2.1.30) and aldehyde dehydrogenase by engineered *E. coli* and native and engineered *Klebsiella* has been reported most extensively (Kwak et al., 2012, Rathnasingh, et al., 2009, Luo et al., 2011, Luo et al., 2012, WO2001/016346).

Expression of active enzymes for conversion of lactate into 3HP has been described in WO02/42418, however this route is thermodynamically unfavorable and likely to result in a mixture of lactate and 3HP. Additionally as hydroxymutase, which could convert lactate directly into 3HP, is not found, an alternative 4-step route via propionate CoA-transferase (E.C. 2.8.3.1), lactoyl-CoA dehydratase (E.C. 4.2.1.54), enoyl-CoA hydratase (E.C. 4.2.1.17) and general CoA-lyase (E.C. 6.2.1.-) or 3-hydroxyisobutyryl-CoA hydrolase (E.C. 3.1.2.4) is used.

Finally the route where beta-alanine is converted into malonyl-semialdehyde either by the action of beta-alanine-pyruvate aminotransferase (E.C. 2.6.1.18) or 3-hydroxyisobutyrate dehydrogenase (E.C. 1.1.1.31) has been reported in *E. coli* (US2007/0107080A1). A process utilizing GabT in a non-conventional yeast has been reported (WO2012/074818). Malonyl-semialdehyde is further reduced into 3HP by the action of HIBADH or HPDH. Beta-alanine is present in the cells a product of aspartate degradation or it can be generated from L-alanine by an engineered 2,3-aminomutase with specificity for L-alanine (US2010/0136638A1).

The metabolic pathways producing 3HP may involve several genes, any and all of which may be exogenous or endogenous to the organism to which the cell of the invention belongs.

Thus, said metabolic pathway preferably comprises the enzyme malonyl-CoA reductase and/or the enzyme malonyl-CoA reductase (malonate semialdehyde-forming) in combination with the enzyme 3-hydroxyisobutyrate dehydrogenase and/or the enzyme hydroxypropionate dehydrogenase.

Said metabolic pathway preferably comprises a malonyl-CoA reductase gene, which may be the malonyl-CoA reductase gene from *Chloroflexus aurantiacus* (CaMCR), and may comprise an acetyl-CoA carboxylase gene. Thus, the metabolic pathway may include both the malonyl-CoA reductase gene from *Chloroflexus aurantiacus* (CaMCR) and the acetyl-CoA carboxylase gene (ACC1) of *S. cerevisiae*.

Optionally said metabolic pathway comprises beta-alanine pyruvate aminotransferase and/or gamma-aminobutyrate transaminase in combination with hydroxyisobutyrate dehydrogenase and/or hydroxypropionate dehydrogenase.

Optionally, said metabolic pathway comprises lactate dehydrogenase, propionate CoA-transferase, lactoyl-CoA dehydratase, enoyl-CoA hydratase and 3-hydroxyisobutyryl-CoA hydrolase.

Optionally, said metabolic pathway comprises glycerol dehydratase and alcohol dehydrogenase.

Optionally, said metabolic pathway comprises the beta-alanine pyruvate aminotransferase from *Bacillus cereus* together with one of the following: 3-hydroxypropanoate dehydrogenase from *Metallosphaera sedula*, 3-hydroxypropanoate dehydrogenase from *Sulfolobus tokadaii*, 3-hydroxypropanoate dehydrogenase from *E. coli* (YdfGp), 3-hydroxypropanoate dehydrogenase from *E. coli* (RutEp), 3-hydroxyisobutyrate dehydrogenase from *Pseudomonas aeruginosa*, 3-hydroxyisobutyrate dehydrogenase from *P. putida*, 3-hydroxyisobutyrate dehydrogenase from *Bacillus cereus*, or 3-hydroxyisobutyrate dehydrogenase from *Candida albicans*.

The cell is preferably a yeast cell, especially a *Saccharomyces cerevisiae* cell. In *Saccharomyces cerevisiae* in particular said genetic modification preferably comprises one or more mutations in gene SFA1 at aa276 Cys and/or at aa283 Met.

However, the invention is not limited in this regard and the cell may be a fungal cell. Examples of fungal cells include, without limitation, *Aspergillus, Fusarium, Neurospora, Penicillium,* and *Trichoderma* taxonomical classes. Examples of suitable yeast include, without limitation, *Saccharomyces, Schizosaccharomyces, Kluyveromyces, Pichia, Candida, Yarrowia, Brettanomyces, Hansenula, Lipomyces,* and *Issatchenkia* taxonomical classes. The cell may also be bacterial rather than fungal and may for instance be of the genus *Eschericia, Lactobacillus, Lactococcus, Corynebacterium, Clostridium,* or *Bacillus*.

The cell may be by way of example *S. cerevisiae, S. pombe, S. kluyveri, K. lactis, K. marxianus, Y. lipolytica, T. delbrueckii, R. minuta, I. orientalis, P. stipites, L. starkeyi, C. guilliermondii,* or *E. coli*.

In a further aspect, the invention provides a yeast exhibiting tolerance for 3HP, said yeast having a mutation in gene SFA1 conferring said tolerance.

Optionally, the yeast is *Saccharomyces cerevisiae* and said mutation in gene SFA1 is at aa276 Cys and/or at aa283 Met.
said mutation in gene SFA1 is Cys276→Ser, Cys276→Val, Cys276→Thr, Cys276→Gly, Cys276→Ala and/or Met276→Ile, Met276→Ala, Met276→Val. In particular, it is preferred that said mutation in gene SFA1 is Cys→Ser (aa276) and/or Met→Ile(aa283).

In a further aspect, the invention includes a method of producing 3HP comprising cultivating a 3HP producing cell under 3HP producing conditions in a culture medium so as to produce 3HP, wherein toxicity of 3HP is reduced by an enhanced activity of 3HP detoxification by a reaction pathway that includes a glutathione-dependent dehydrogenase reaction.

The enhanced activity of said pathway may be provided by genetic modification as described above but additionally or alternatively may be provided by said culture medium being supplemented with glutathione and/or cysteine, glutamate, glycine, serine, methionine, and arginine (Wen et al., 2004).

Preferably, glutathione is added to the culture medium to produce a concentration therein of >2.5 mM.

Instead or additional to addition of glutathione, the cell may have a genetic modification conferring an enhanced glutathione production ability thereon. This may be such that the cell overexpresses the glutathione biosynthetic genes gamma-glutamylcysteine synthetase and glutathione synthetase. Alternatively or additionally it may be such that the cell overexpresses genes that enhance the production of amino acid precursors for glutathione biosynthesis.

In view of the enhanced 3HP tolerance of the cells, the concentration of 3HP in the culture medium may be permitted to rise to in excess of 1 g/l, e.g. in excess of 3, or 4 or 5 g/l or 10 g/l.

In a further aspect, the invention provides the use of an enhanced glutathione-dependent dehydrogenase reaction in a cell to enhance tolerance of said cell to 3HP.

Optionally, reaction is one converting S-(3-hydroxypropanoyl)glutathione to S-(3-ketopropanoyl)glutathione.

DESCRIPTION OF THE DRAWINGS

The invention will be further described and illustrated with reference to the accompanying drawings in which.

EXAMPLES

Figure 1:
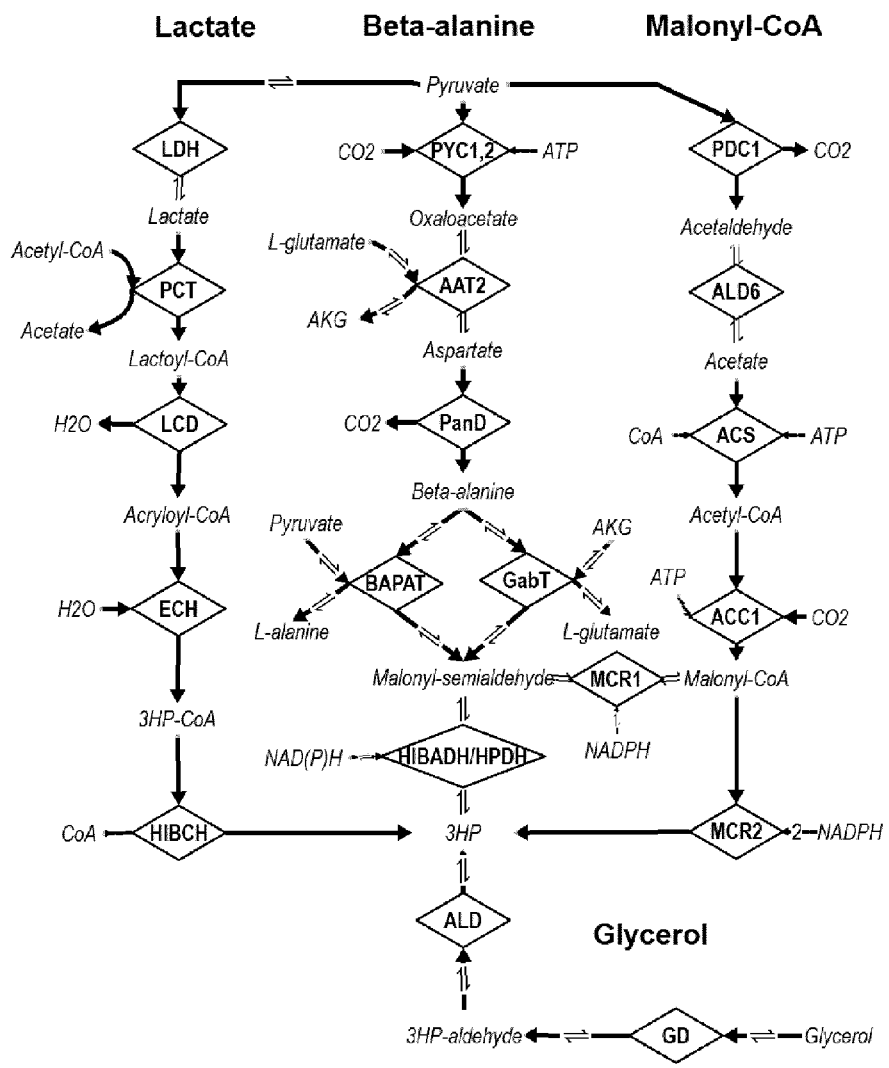
FIG. 1 illustrates pathways leading from pyruvate to 3HP; The following abbreviations are used:
PYC—pyruvate carboxylase,
AAT—aspartate aminotransferase,
PanD—aspartate decarboxylase,
BAPAT—beta-alanine pyruvate aminotransferase,
GabT—gamma-aminobutyrate transaminase,
HIBADH—3-hydroxyisobutyrate dehydrogenase,
HPDH—hydroxypropionate dehydrogenase,
HPDH—3-hydroxypropionate dehydrogenase,
LDH—lactate dehydrogenase,
PCT—propionate CoA-transferase,
LCD—lactoyl-CoA dehydratase,
ECH—enoyl-CoA hydratase,
HIBCH—3-hydroxyisobutyryl-CoA hydrolase.
MCR1—malonyl-CoA reductase (malonate semialdehyde-forming),
MCR2—bi-functional malonyl-CoA reductase,
GD—glycerol dehydratase,
ALD—aldehyde dehydrogenase

The following examples demonstrate the effectiveness of the invention. The following tables summarise materials used in the Examples and results obtained.

TABLE 1

Primers

| Primer name | Primer sequence, 5'->3' | SEQ ID NO |
|---|---|---|
| KO_sfa1_fw | CAGAATTTGTTGGCCTATTTTCTTA | SEQ ID NO 16 |
| KO_sfa1_rv | CAATACGTTGGTAGTTAGGAACAGG | SEQ ID NO 17 |
| KO_sfa1_test_fw | GATGCTCATCACAGACTACT | SEQ ID NO 18 |
| KanMX_2/3_START_rv | AGTGACGACTGAATCCGGTG | SEQ ID NO 19 |
| PTEF1_fw | ACCTGCACUTTGTAATTAAAACTTAG | SEQ ID NO 20 |
| PTEF1_rv | CACGCGAUGCACACACCATAGCTTC | SEQ ID NO 21 |
| SFA1_U1_fw | AGTGCAGGUAAAACAATGTCCGCCGCTACTGTT | SEQ ID NO 22 |
| SFA1_U1_rv | CGTGCGAUTCATTTTATTTCATCAGACTTCAAGA | SEQ ID NO 23 |
| SFA1_UPrevU1 | AGCTGTTCUCTATTTTATTTCATCAGACTTCAAGACG | SEQ ID NO 24 |
| SFA1_DWfwd_U2 | AGTGGCCUGAGTACTTAATTAAACTAAGTAAGCATGACTC | SEQ ID NO 25 |
| KO-SFA1_UPrev2 | GTCTACCGTGATTTCTTCAACACTT | SEQ ID NO 26 |
| NB336K1LEUFwd1 | TGGAAGAGGCAAGCACGTTAGC | SEQ ID NO 27 |
| NB335K1LEURev1 | CAGAAGCATAACTACCCATTCC | SEQ ID NO 28 |
| NB326URA3fwdU | AGAACAGCUGAAGCTTCGTACG | SEQ ID NO 29 |
| NB327URA3Rev2U | AGGCCACUAGTGGATCTGATATCAC | SEQ ID NO 30 |
| PPGK1_rv | CACGCGAUGCACACACCATAGCTTC | SEQ ID NO 31 |
| gsh1_U1_fw | AGTGCAGGUAAAACAATGGGACTCTTAGCTTTGGG | SEQ ID NO 32 |
| gsh1_U1_rv | CGTGCGAUTCAACATTTGCTTTCTATTGAAGGC | SEQ ID NO 33 |
| gsh2_U1_fw | ATCTGTCAUAAAACAATGGCACACTATCCACCTTCC | SEQ ID NO 34 |
| gsh2_U1_rv | CACGCGAUTCAGTAAAGAATAATACTGTCC | SEQ ID NO 35 |
| met14_U1_fw | AGTGCAGGUAAAACAATGGCTACTAATATTACTTGGC | SEQ ID NO 36 |
| met14_U1_rv | CGTGCGAUTCACAAATGCTTACGGATGATTTTTTC | SEQ ID NO 37 |
| met16_U1_fw | ATCTGTCAUAAAACAATGAAGACCTATCATTTG | SEQ ID NO 38 |
| met16_U1_ev | CACGCGAUTCAGGCATCTTGCTTTAAAAATTGC | SEQ ID NO 39 |
| SFA1_G614C_fw | ATACCGTTGCAGTATTTGGCTCCGGGACTGTAG | SEQ ID NO 40 |
| SFA1_G614C_rv | CTACAGTCCCGGAGCCAAATACTGCAACGGTAT | SEQ ID NO 41 |
| SFA1_G710C_fw | GCCATTGACATTAACAATAAGAAAAAACAATATTCTTCTCAATTTGGTGCCAC | SEQ ID NO 42 |
| SFA1_G710C_rv | GTGGCACCAAATTGAGAAGAATATTGTTTTTTCTTATTGTTAATGTCAATGGC | SEQ ID NO 43 |

TABLE 1-continued

Primers

| Primer name | Primer sequence, 5'->3' | SEQ ID NO |
|---|---|---|
| SFA1_G869C_fw | GAGAGATGCTTTGGAAGCCTCTCATAAAGGTTGGG | SEQ ID NO 44 |
| SFA1_G869C_rv | CCCAACCTTTATGAGAGGCTTCCAAAGCATCTCTC | SEQ ID NO 45 |
| SFA1_T826G_fw | GGGGTCTGGATTTTACTTTTGACGGTACTGGTAATACCAAAATTATG | SEQ ID NO 46 |
| SFA1_T826G_rv | CATAATTTTGGTATTACCAGTACCGTCAAAAGTAAAATCCAGACCCC | SEQ ID NO 47 |
| SFA1_TG826GC_fw | GGGGTCTGGATTTTACTTTTGACGCTACTGGTAATACCAAAATTATG | SEQ ID NO 48 |
| SFA1_TG826GC_rv | CATAATTTTGGTATTACCAGTAGCGTCAAAAGTAAAATCCAGACCCC | SEQ ID NO 49 |
| SFA1_TG826GT_fw | GGGGGTCTGGATTTTACTTTTGACGTTACTGGTAATACCAAAATTATGAG | SEQ ID NO 50 |
| SFA1_TG826GT_rv | CTCATAATTTTGGTATTACCAGTAACGTCAAAAGTAAAATCCAGACCCCC | SEQ ID NO 51 |
| SFA1_T826A_fw | GGGGTCTGGATTTTACTTTTGACACTACTGGTAATACCAAAATTATG | SEQ ID NO 52 |
| SFA1_T826A_rv | CATAATTTTGGTATTACCAGTAGTGTCAAAAGTAAAATCCAGACCCC | SEQ ID NO 53 |
| SFA1_A847G_fw | CTTTTGACTGTACTGGTAATACCAAAATTGTGAGAGATGCTTTGG | SEQ ID NO 54 |
| SFA1_A847G_rv | CCAAAGCATCTCTCACAATTTTGGTATTACCAGTACAGTCAAAAG | SEQ ID NO 55 |
| SFA1_AT847GC_fw | TTACTTTTGACTGTACTGGTAATACCAAAATTGCGAGAGATGCTTTGGAAG | SEQ ID NO 56 |
| SFA1_AT847GC_rv | CTTCCAAAGCATCTCTCGCAATTTTGGTATTACCAGTACAGTCAAAAGTAA | SEQ ID NO 57 |

TABLE 2

Primers and templates used to generate gene fragments for gene reaplcement

| Fragment name | Gene | Fw_primer | Rv_primer | Template DNA |
|---|---|---|---|---|
| SFA1_UP | Upstream region of SFA1 | KO_sfa1_fw | KO-SFA1_UPrev2 | gDNA of S. cerevisiae |
| SFA1wt_UP | Upstream region of SFA1 including SFA1-wt | KO_sfa1_fw | SFA1_UPrevU1 | gDNA of S. cerevisiae |
| SFA1$^{G827C}$_UP | SFA1 upstream region fused by PCR to the SFA1$^{G827C}$ gene | KO_sfa1_fw | SFA1_UPrevU1 | Fragment SFA1_UP_wt and SFA1$^{G827C}$ |
| SFA1G$^{849A}$_UP | SFA1 upstream region fused by PCR to the SFA1$^{G849A}$ gene | KO_sfa1_fw | SFA1_UPrevU1 | Fragment SFA1_UP_wt and SFA1$^{G849A}$ |
| SFA1_DOWN | Downstream region of SFA1 | SFA1_DWfwd_U2 | SFA1_DW_test_rv | gDNA of S. cerevisiae |
| LEU2_U_2/3_START | the first ⅔ of loxP-KlLEU2 marker | NB326URA3fwdU | NB335KlLEURev1 | Plasmid pUG73 |
| LEU2_U_2/3_END | the last ⅔ part of loxP-KlLEU2 marker | NB336KlLEUFwd1 | NB327URA3Rev2U | Plasmid pUG73 |
| SFA1wt_UP_LEU2_U_2/3_START | SFA1 upstream region including SFA1-wt fused by PCR to the first ⅔ of KlLEU2 marker | KO_sfa1_fw | NB335KlLEURev1 | Fragment SFA1_UP_wt and LEU2_U_2/3_START |
| SFA1$^{G827C}$_UP_LEU2_U_2/3_START | SFA1 upstream region including SFA1$^{G827C}$ fused by PCR to the first ⅔ of KlLEU2 marker | KO_sfa1_fw | NB335KlLEURev1 | Fragment SFA1$^{G827C}$_UP and LEU2_U_2/3_START |
| SFA1$^{G849A}$_UP_LEU2_U_2/3_START | SFA1 upstream region including SFA1$^{G849A}$ fused by PCR to the first ⅔ of KlLEU2 marker | KO_sfa1_fw | NB335KlLEURev1 | Fragment SFA1$^{G849A}$_UP and LEU2_U_2/3_START |
| LEU2_U_2/3_END_SFA1_DOWN | the last part of KlLEU2 marker fused by PCR to SFA1 downstream region | NB336KlLEUFwd1 | SFA1_DW_test_rv | Fragment LEU2_U_2/3_END and SFA1_DOWN |
| SFA1$^{G614C}$ | SFA1 gene where nt 614 was changed from G to C (Cys205Ser) | SFA1_U1_fw | SFA1_U1_rv | pESC-LEU-SFA1$^{G614C}$ |
| SFA1$^{G710C}$ | SFA1 gene where nt 710 was changed from G to C (Cys237Ser) | SFA1_U1_fw | SFA1_U1_rv | pESC-LEU-SFA1$^{G710C}$ |
| SFA1$^{G869C}$ | SFA1 gene where nt 869 was changed from G to C (Cys290Ser) | SFA1_U1_fw | SFA1_U1_rv | pESC-LEU-SFA1$^{G869C}$ |

TABLE 2-continued

Primers and templates used to generate gene fragments for gene reaplcement

| Fragment name | Gene | Fw_primer | Rv_primer | Template DNA |
|---|---|---|---|---|
| SFA1$^{T826G}$ | SFA1 gene where nt 826 was changed from T to G (Cys276Gly) | SFA1_U1_fw | SFA1_U1_rv | pESC-LEU-SFA1$^{T826G}$ |
| SFA1$^{TG826GC}$ | SFA1 gene where nt 826 and 827 were changed from T to G and G to C, respectively (Cys276Ala) | SFA1_U1_fw | SFA1_U1_rv | pESC-LEU-SFA1$^{TG826GC}$ |
| SFA1$^{TG826GT}$ | SFA1 gene where nt 826 and 827 were changed from T to G and G to T, respectively (Cys276Val) | SFA1_U1_fw | SFA1_U1_rv | pESC-LEU-SFA1$^{TG826GT}$ |
| SFA1$^{TG826AC}$ | SFA1 gene where nt 826 and 827 were changed from T to A and G to C, respectively (Cys276Thr) | SFA1_U1_fw | SFA1_U1_rv | pESC-LEU-SFA1$^{TG826AC}$ |
| SFA1$^{A847G}$ | SFA1 gene where nt 847 was changed from A to G (Met283Val) | SFA1_U1_fw | SFA1_U1_rv | pESC-LEU-SFA1$^{A847G}$ |
| SFA1$^{AT847GC}$ | SFA1 gene where nt 847 and 848 were changed from A to G and T to C, respectively (Met283Ala) | SFA1_U1_fw | SFA1_U1_rv | pESC-LEU-SFA1$^{AT847GC}$ |
| SFA1$^{G614C}$_UP_LEU2_U_2/3_START | SFA1 upstream region fused by PCR to the including SFA1$^{G614C}$ gene and the first 2/3 of KlLEU2 marker | KO_sfa1_fw | NB335KlLEURev1 | Fragment SFA1_UP, SFA1$^{G614C}$ and LEU2_U_2/3_START |
| SFA1$^{G710C}$_UP_LEU2_U_2/3_START | SFA1 upstream region fused by PCR to the including SFA1$^{G710C}$ gene and the first 2/3 of KlLEU2 marker | KO_sfa1_fw | NB335KlLEURev1 | Fragment SFA1_UP, SFA1$^{G710C}$ and LEU2_U_2/3_START |
| SFA1$^{G869C}$_UP_LEU2_U_2/3_START | SFA1 upstream region fused by PCR to the including SFA1$^{G869C}$ gene and the first 2/3 of KlLEU2 marker | KO_sfa1_fw | NB335KlLEURev1 | Fragment SFA1_UP, SFA1$^{G869C}$ and LEU2_U_2/3_START |
| SFA1$^{T826C}$_UP_LEU2_U_2/3_START | SFA1 upstream region fused by PCR to the including SFA1$^{T826C}$ gene and the first 2/3 of KlLEU2 marker | KO_sfa1_fw | NB335KlLEURev1 | Fragment SFA1_UP, SFA1$^{T826C}$ and LEU2_U_2/3_START |
| SFA1$^{TG826Gc}$_UP_LEU2_U_2/3_START | SFA1 upstream region fused by PCR to the including SFA1$^{TG826GC}$ gene and the first 2/3 of KlLEU2 marker | KO_sfa1_fw | NB335KlLEURev1 | Fragment SFA1_UP, SFA1$^{TG826GC}$ and LEU2_U_2/3_START |
| SFA1$^{TG826GT}$_UP_LEU2_U_2/3_START | SFA1 upstream region fused by PCR to the including SFA1$^{TG826GT}$ gene and the first 2/3 of KlLEU2 marker | KO_sfa1_fw | NB335KlLEURev1 | Fragment SFA1_UP, SFA1$^{TG826GT}$ and LEU2_U_2/3_START |
| SFA1$^{TG826AC}$_UP_LEU2_U_2/3_START | SFA1 upstream region fused by PCR to the including SFA1$^{TG264AC}$ gene and the first 2/3 of KlLEU2 marker | KO_sfa1_fw | NB335KlLEURev1 | Fragment SFA1_UP, SFA1$^{TG826AC}$ and LEU2_U_2/3_START |
| SFA1$^{A847C}$_UP_LEU2_U_2/3_START | SFA1 upstream region fused by PCR to the including SFA1$^{A847C}$ gene and the first 2/3 of KlLEU2 marker | KO_sfa1_fw | NB335KlLEURev1 | Fragment SFA1_UP, SFA1$^{A847C}$ and LEU2_U_2/3_START |
| SFA1$^{AT847GC}$_UP_LEU2_U_2/3_START | SFA1 upstream region fused by PCR to the including SFA1$^{AT847G}$ gene and the first 2/3 of KlLEU2 marker | KO_sfa1_fw | NB335KlLEURev1 | Fragment SFA1_UP, SFA1$^{AT847GC}$ and LEU2_U_2/3_START |

TABLE 3

Primers and templates used to generate gene fragments for USER cloning by PCR

| Fragment name | Gene | Fw_primer | Rv_primer | Template DNA |
|---|---|---|---|---|
| PTEF1 | Promoter of TEF1 gene from S. cerevisiae | PTEF1_fw | PTEF1_rv | gDNA of S. cerevisiae |

TABLE 3-continued

Primers and templates used to generate gene fragments for USER cloning by PCR

| Fragment name | Gene | Fw_primer | Rv_primer | Template DNA |
|---|---|---|---|---|
| SFA1-wt | SFA1 gene (WT sequence) | SFA1_U1_fw | SFA1_U1_rv | gDNA of S. cerevisiae |
| SFA1$^{G827C}$ | SFA1 gene where nt 827 was changed from G to C | SFA1_U1_fw | SFA1_U1_rv | gDNA of S. cerevisiae |
| SFA1$^{G849A}$ | SFA1 gene where nt 849 was changed from G to A | SFA1_U1_fw | SFA1_U1_rv | gDNA of S. cerevisiae |
| <-PTEF1-PPGK1-> | Fused promoters of TEF1 and PGK1 genes from S. cerevisiae | PTEF1_fw | PPGK1_rv | plasmid pSP-GM1 |
| GSH1<- | Gamma glutamylcysteine synthetase (GSH1) from S. cerevisiae | gsh1_U1_fw | gsh2_U1_rv | gDNA of S. cerevisiae |
| GSH2-> | Glutathione synthetase (GSH2) from S. cerevisiae | gsh1_U1_fw | gsh2_U1_rv | gDNA of S. cerevisiae |
| MET14<- | Adynylylsulfate kinase (MET14) from S. cerevisiae | gsh1_U1_fw | met14_U1_rv | gDNA of S. cerevisiae |
| MET16-> | 3'-phosphoadenylsulfate reductase (MET16) from S. cerevisiae | met16_U1-fw | met16_U1-rv | gDNA of S. cerevisiae |

TABLE 4

Plasmids

| Plasmid name | Parent plasmid | Selection marker | Cloned fragment | Promoter | Terminator |
|---|---|---|---|---|---|
| pESC-LEU | | LEU2 | — | — | — |
| pESC-LEU-USER | | LEU2 | — | — | — |
| pUG73 | | KlLEU2 | — | — | — |
| pESC-LEU-SFA1-wt | pESC-LEU-USER | LEU2 | SFA1-wt | PTEF1 | TADH1 |
| pESC-LEU-SFA1$^{G827C}$ | pESC-LEU-USER | LEU2 | SFA1$^{G827C}$ | PTEF1 | TADH1 |
| pESC-LEU-SFA1$^{G849A}$ | pESC-LEU-USER | LEU2 | SFA1$^{G849A}$ | PTEF1 | TADH1 |
| pESC-URA | | | | | |
| pESC-URA-USER | | | | | |
| pESC-URA-GSH1-GSH2 | pESC-URA-USER | | | | |
| pESC-HIS | | | | | |
| pESC-HIS-USER | | | | | |
| pESC-HIS-MET14-MET16 | pESC-HIS-USER | | | | |
| pESC-LEU-SFA1$^{G614C}$ | pESC-LEU-USER | | | | |
| pESC-LEU-SFA1$^{G710C}$ | pESC-LEU-USER | | | | |
| pESC-LEU-SFA1$^{G869C}$ | pESC-LEU-USER | | | | |
| pESC-LEU-SFA1$^{T826G}$ | pESC-LEU-USER | | | | |
| pESC-LEU-SFA1$^{TG826GC}$ | pESC-LEU-USER | | | | |
| pESC-LEU-SFA1$^{TG826GT}$ | pESC-LEU-USER | | | | |
| pESC-LEU-SFA1$^{T826A}$ | pESC-LEU-USER | | | | |
| pESC-LEU-SFA1$^{A847G}$ | pESC-LEU-USER | | | | |
| pESC-LEU-SFA1$^{AT847GC}$ | pESC-LEU-USER | | | | |

TABLE 5

Yeast strains

| Strain name | Genotype |
|---|---|
| CEN.PK 113-7D | MATa URA3 HIS3 LEU2 TRP1 |
| CEN.PK 113-32D | MATa leu2Δ |
| CEN.PK 102-5B | MATa ura3Δ leu2Δ his3Δ |
| sfa1Δ | MATa leu2Δ sfa1::KanMX |
| SCE-R1-48 | MATa leu2Δ sfa1::KanMX + pESC-LEU |
| SCE-R1-49 | MATa leu2Δ sfa1::KanMX + pESC-LEU-SFA1-wt |
| SCE-R1-50 | MATa leu2Δ sfa1::KanMX + pESC-LEU-SFA1$^{G827C}$ |
| SCE-R1-51 | MATa leu2Δ sfa1::KanMX + pESC-LEU-SFA1$^{G849A}$ |
| ST609 | MATa leu2Δ sfa1::SFA1-wt:KlLEU2 |
| ST610 | MATa leu2Δ sfa1::SFA1$^{G821C}$:KlLEU2 |
| ST611 | MATa leu2Δ sfa1::SFA1$^{G849A}$:KlLEU2 |
| ST637 | MATa leu2Δ ACC1-CaMCR:KlURA3 ACSse-ALD6:KlLEU2 PDC1:SpHIS5 |
| ST726 | MATa ura3Δ leu2Δ his3Δ sfa1:: SFA1$^{G827C}$:KlLEU2 |
| ST727 | MATa ura3Δ leu2Δ his3Δ sfa1:: SFA1$^{G849A}$:KlLEU2 |
| ST728 | MATa ura3Δ leu2Δ his3Δ sfa1:: SFA1wt:KlLEU2 |

TABLE 6

Strains and 3HP titers in strains producing 3HP via malonyl-CoA pathway

| Strain name | Parent strain | Plasmid with LEU2 marker | 3HP titer (g/L) in Delft media | 3HP titer (g/L) in FIT media |
|---|---|---|---|---|
| wt | CEN.PK113-7D | — | 0.1 ± 0.01 | 0.4 ± 0.02 |
| R2-129 | ST637 | pESC-LEU | 1.8 ± 0.4 | 5.4 ± 0.9 |
| R2-130 | ST637 | pESC-LEU-SFA1-wt | 2.1 ± 0.4 | 5.9 ± 1.0 |
| R2-131 | ST637 | pESC-LEU-SFA1$^{G827C}$ | 1.8 ± 0.4 | 5.7 ± 0.5 |
| R2-132 | ST637 | pESC-LEU-SFA1$^{G849A}$ | 2.0 ± 0.2 | 5.8 ± 0.9 |

Example 1. Toxicity of 3-Hydroxypropionic Acid (3HP)

The toxicity of 3HP on growth of S. cerevisiae CEN.PK 113-7D strain (WT) was determined by evaluating the ability of the WT strain to grow on a chemically defined minimal medium (Delft) containing varying concentrations of 3HP (0-100 g/L). The composition of Delft medium was as follows: 20.0 g/L glucose, 5.0 g/L $(NH_4)_2SO_4$, 3.0 g/L $KH_2PO_4$, 0.5 g/L $MgSO_4.7H_2O$, 1.0 mL/L trace metal solution, 0.05 g/L antifoam A (10794, Sigma-Aldrich), and 1.0 mL/L vitamin solution. The trace element solution included 15 g/L EDTA, 0.45 g/L $CaCl_2.2H_2O$, 0.45 g/L $ZnSO_4.7H_2O$, 0.3 g/L $FeSO_4.7H_2O$, 100 mg/L $H_3BO_4$, 1 g/L $MnCl_2.2H_2O$, 0.3 g/L $CoCl_2.6H_2O$, 0.3 g/L $CuSO_4.5H_2O$, 0.4 g/L $NaMoO_4.2H_2O$. The pH of the trace metal solution was adjusted to 4.0 with 2 M NaOH and heat sterilized. The vitamin solution included 50 mg/L d-biotin, 200 mg/L para-amino benzoic acid, 1 g/L nicotinic acid, 1 g/L Ca.pantothenate, 1 g/L pyridoxine HCl, 1 g/L thiamine HCl, and 25 mg/L m. inositol. The pH of the vitamin solution was adjusted to 6.5 with 2 M NaOH, sterile-filtered and the solution was stored at 4° C. The Delft medium was prepared as a concentrate solution and the pH was adjusted to 6.0 and sterilized by autoclaving. Glucose was autoclaved separately. The final Delft medium (Delft buffered) was obtained by adding 79.5 mL of 0.5 M citrate solution (105 g/L $C_6H_8O_7.H_2O$) and 20.5 mL of 1M sodium phosphate solution (178 g/L $Na_2HPO_4.2H_2O$) to control the pH of the medium at pH 3.5. For media containing 3HP, the 3HP solution (ca. 30% in water; Tokyo Chemical Industry Co.) was neutralized with solid NaOH (0.133 g NaOH/1 mL of 3HP solution) and sterile-filtered before adding to the Delft buffered media.

Figure 2:
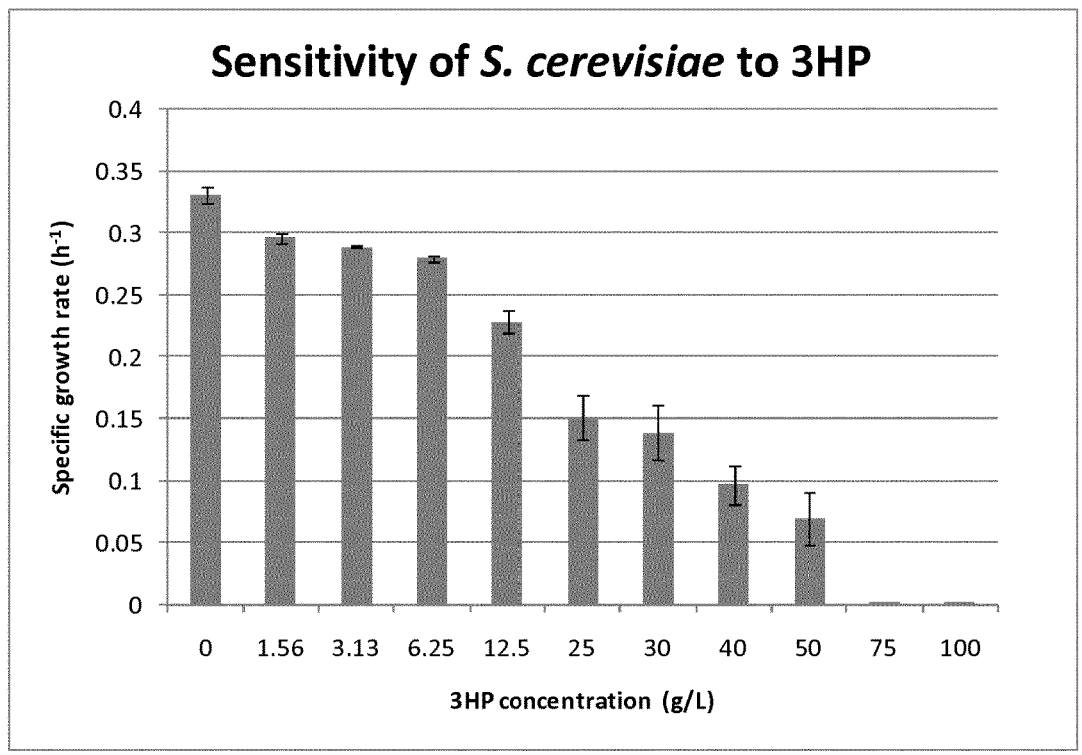
FIG. 2 shows growth curves for *S. cerevisiae* on minimal medium in the presence of different concentrations of 3HP, as described in Example 1.

A single colony from YPD plate (10 g/L yeast extract, 20 g/L peptone, 20 g/L glucose and 20 g/L agar) was inoculated in a shake flask with 20 mL YPD broth and grown at 30° C., with shaking at 200 rpm, overnight. The absorbance ($OD_{600}$) of the overnight culture was measured at 600 nm wave length using NanoPhotometer™ UV/Vis (Implen) and the culture was diluted with YPD medium to obtain inoculum with the $OD_{600}$ around 0.8. The diluted culture was used to inoculate 100 µL Delft buffered medium (pH 3.5) containing various concentration of 3HP (0-100 g/L) in 96-well flat bottom plate (Greiner) with the starting inoculum of $OD_{600}$=0.04. The 96-well plate was incubated at 30° C. with shaking in the Synergy™ MX microplate reader (BioTek) and the absorbance was measured at 600 nm wavelength every 15 min for 42 hours. Experiments were done in duplicates, and the specific growth rate ($h^{-1}$) was calculated at various concentrations of 3HP. The resulting of 3HP sensitivity is shown in FIG. 2.

It can be seen that any concentration of 3-HP much above 10 g/L produces a substantial level of inhibition and the wild type yeast is unable to grow at all in concentrations of 75 g/L.

Example 2. Metabolic Engineering for Improving 3HP Tolerance in S. cerevisae

A strain with SFA1 deletion was constructed and tested for 3HP tolerance. In addition, three versions of the SFA1 gene (native and two alleles) were overexpressed in the sfa1Δ and WT strains and 3HP tolerance was investigated. Deletion of SFA1 did not result in any 3HP tolerance. However, overexpression of SFA1 gene (native and two alleles) enabled growth on 50 g/L 3HP of the WT and sfa1Δ strains. The two alleles are referred to herein as SFA1$^{G827C}$ (Cys→Ser(aa276)) and SFA1$^{G849A}$ (Met→Ile(aa283)).

The sfa1Δ strain was constructed by replacing the target gene in the CEN.PK113-32D strain with the KanMX cassette.

The gene fragments carrying the KanMX cassette and correct overhangs for SFA1 replacement (KO-SFA1) was generated by PCR amplification using primers and template as indicated in Table 2. The PCR mix contained: 31 µl water, 10 µl high fidelity Phusion® polymerase buffer (5×), 5 µl 2 mM dNTP, 1 µl Phusion® polymerase, 1 µl forward primer at 10 µM concentration, 1 µl reverse primer at 10 µM concentration, and 1 µl DNA template. The cycling program was: 95° C. for 2 min, 30 cycles of [95° C. for 10 sec, 50° C. for 20 sec, 68° C. for 1 min], 68° C. for 5 min, pause at 10° C. The gene fragments were resolved on 1% agarose gel containing SYBR®-SAFE (Invitrogen) and purified using NucleoSpin® Gel and PCR Clean-up kit (Macherey-Nagel).

The KO-SFA1 fragment was transformed into S. cerevisiae cells using the lithium acetate transformation protocol. The cells were selected on YPD plate with G418 (200 µg/mL). The transformants were streak purified on YPD+G418 plate in order to obtain single colonies. The correct transformants were confirmed by PCR analysis using primers KO_sfa1_test_fw/KanMX_2/3_START_rv.

To construct the overexpression plasmid containing SFA1 gene, the SFA1-wt (SEQ ID NO 1), SFA1$^{G827C}$ (SEQ ID NO 2), SFA1$^{G849A}$ (SEQ ID NO 3) genes were subcloned into pESC-LEU-USER plasmid by USER cloning. The final plasmids (Table 4) were then transformed into different background strains (WT and sfa1Δ) using the lithium acetate transformation protocol and selected on synthetic complete agar medium without leucine (SC-Leu). Transformants were streaked purified on SC-Leu to obtain single colonies. The resulting strains are listed in Table 5.

The promoter fragment (PTEF1, SEQ ID 4) was generated by PCR followed by gene purification (Table 3). The terminators were already present on the expression plasmids.

The parent plasmid pESC-LEU-USER were linearized with FastDigest® AsiSI (Fermentas) for 1 hour at 37° C. and nicked with Nb.BsmI for 1 hour at 37° C. The resulting linearized nicked DNA was purified from the solution and eluted in 5 mM Tris buffer, pH 8.0.

The expression plasmids were created by USER-cloning using the following protocol. One µl of linearized and nicked parent plasmid was mixed with 1 µL of promoter fragment, 2 µL of gene fragment, 0.5 µL Taq polymerase buffer, 0.5 µL USER enzyme (NEB). The mix was incubated at 37° C. for 25 min, at 25° C. for 25 min and transformed into chemically competent *E. coli* DH5alpha. The clones with correct inserts were identified by colony PCR and the plasmids were isolated from overnight *E. coli* cultures and confirmed by sequencing. The expression plasmids are listed in Table 4. For testing 3HP tolerance phenotype, four single colonies from each strain line were investigated for the ability to grow on media containing 3HP. The pre-cultures were prepared by inoculation a single colony in 100 µL SC-Leu media in 96-well flat bottom plate. The plate was incubated at 30° C. with 250 rpm agitation at 5 cm orbit cast overnight. Five µL of the overnight cultures were used to inoculate 100 µL Delft buffered (pH 3.5) containing 50 g/L 3HP. The 96-well plate was incubated at 30° C. with shaking in the Synergy™ MX microplate reader (BioTek) and the absorbance was measured at 600 nm wavelength every 15 min for 42 hours. Experiments were done in triplicate. The resulting improvement in 3HP tolerance in the engineered strains is shown in FIG. 3.

Figure 3:
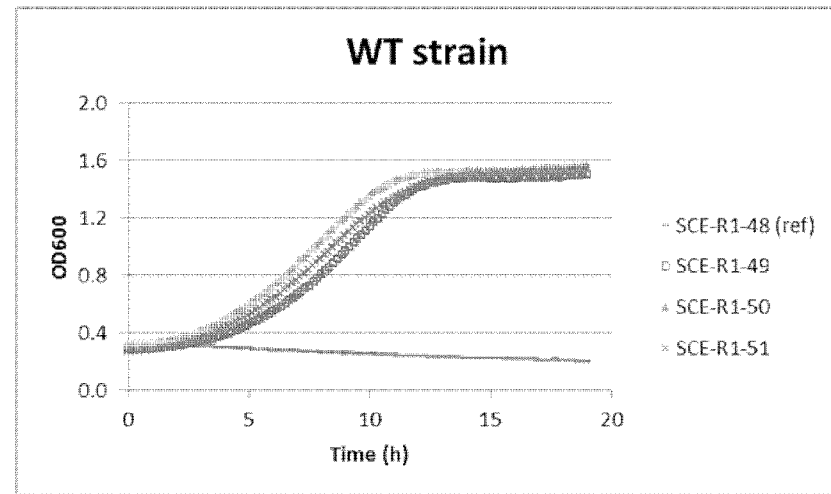
FIG. 3 shows improved 3HP tolerance of strains of *S. cerevisiae* having overexpressed native or mutated SFA1 genes as found in Example 2.
Figure 3:
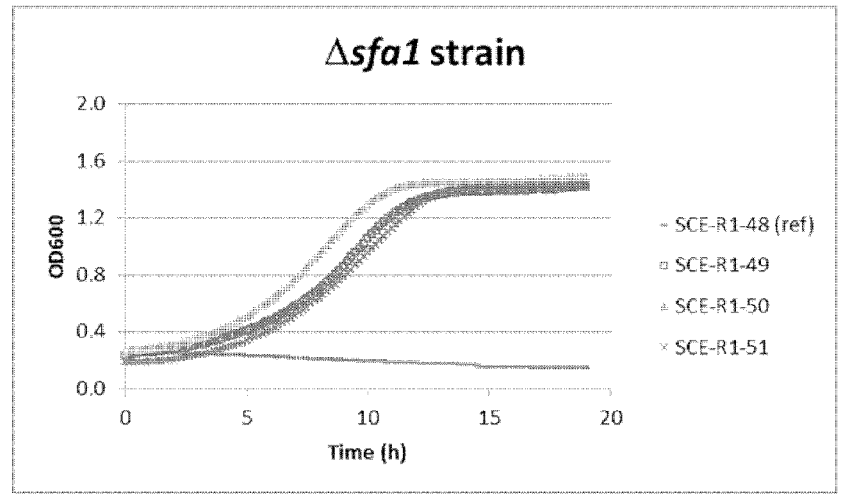

In FIG. 3, SCE-R1-48 is the sfa1Δ strain carrying the empty plasmid pESC-LEU. SCE-R1-49, SCE-R1-50, and SCE-R1-51 are the strains overexpressing SFA1 in its wild type form, SFA1$^{G827C}$, and SFA1$^{G849A}$, respectively. As seen in FIG. 3, all three strains overexpressing a form of SFA1 have improved 3HP tolerance compared to the sfa1Δ strain.

Example 3. Improving 3HP Tolerance in *S. cerevisiae* by Replacing the Native SFA1 with Either SFA1$^{G827C}$ or SFA1$^{G849A}$ To investigate whether only the SFA1 alleles can confer 3HP tolerance without overexpression, the native SFA1 gene was replaced by either SFA1$^{G827C}$ or SFA1$^{G849A}$ and tested for 3HP tolerance. By replacing the SFA1-wt with SFA1$^{G827C}$ or SFA1$^{G849A}$, the constructed strains (ST610 and ST611) could grow on minimum media containing 3HP above 40 g/L, whereas the strain with the SFA1-wt allele without over expression (ST609) could not grow under these conditions. The results clearly showed that only one amino acid changed in SFA1 is enough for *S. cerevisiae* to confer 3HP tolerance.

To generate the substrates for SFA1 allele replacement, the upstream fragment including the SFA1 allele for each SFA1 mutations was generated by fusion PCR using the SFA1 upstream region (SFA1-UP), SFA1-allele fragment and the first part of ⅔ KlLEU2 marker as templates and using primers KO_sfa1_fw and NB335KlLEURev1 (Table 2). The downstream fragment was generated by fusion PCR using the last part of ⅔ KlLEU2 marker and the SFA1 downstream region (SFA1_DOWN) as templates and using primers NB336KlLEUFwd1 and SFA1_DW_test_rv. The cycling program was: 98° C. for 2 min, 30 cycles of [98° C. for 10 sec, 55° C. for 30 sec, 68° C. for 1 min 30 sec], 68° C. for 12 min, pause at 10° C.

The strain with SFA1$^{G827C}$ allele replacement was constructed by replacing the KanMX cassette in the sfa1Δ strain using SFA1$^{G827C}$_UP_LEU2_U_2/3_START and LEU2_U_2/3_END_SFA1_DOWN_wt fragments, whereas the SFA1$^{G849A}$ strain was constructed in the same manner using SFA1$^{G849A}$_UP_LEU2_U_2/3_START and LEU2_U_2/3_END_SFA1_DOWN_wt fragments. For the control strain, the SFA1-wt allele was introduced back to the sfa1Δ strain by using SFA1 wt_UP_LEU2_U_2/3_START and LEU2_U_2/3_END_SFA1_DOWN_wt fragments. The strains were selected on SC-Leu media. The transformants were streaked purified on SC-Leu to obtain single colonies. The correct transformants were confirmed by PCR analysis using primers KO_sfa1_test_fw and SFA1_U1-rv.

Figure 4:
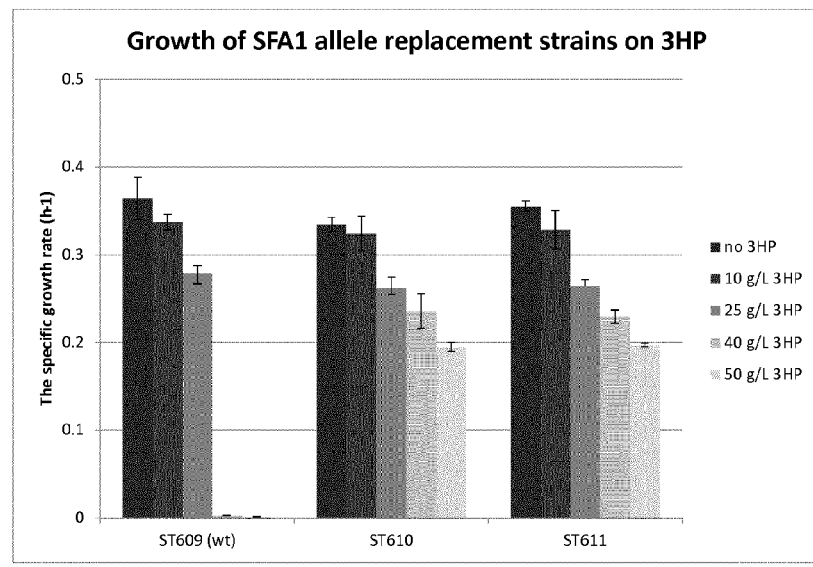
FIG. 4 shows improved 3HP tolerance of strains of *S. cerevisiae* having mutated SFA1 genes at varying levels of 3HP in the minimal medium, as found in Example 3.

For testing 3HP tolerance phenotype, two single colonies from each strain: ST609 (SFA1-wt), ST610 (SFA1$^{G827C}$) and ST611 (SFA1$^{G849A}$) were investigated for the ability to grow on media containing 3HP. The pre-cultures were prepared by inoculation of a single colony in 0.5 mL Delft buffered (pH 3.5) media in 24-well plate. The plate was incubated at 30° C. with 250 rpm agitation at 5 cm orbit cast overnight. Five µL of the overnight cultures were used to inoculate 100 µL Delft buffered (pH 3.5) containing various concentration of 3HP (0, 10, 25, 40 and 50 g/L) in 96-well flat bottom plate. The 96-well plate was incubated at 30° C. with shaking in the Synergy™ MX microplate reader (BioTek) and the absorbance was measured at 600 nm wavelength every 15 min for 42 hours. Experiments were done in duplicates. The resulting of 3HP tolerance in the engineered strains is shown in FIG. 4.

Example 4. Production of 3-Hydroxypropionic Acid Via Malonyl-CoA Pathway

Figure 5:
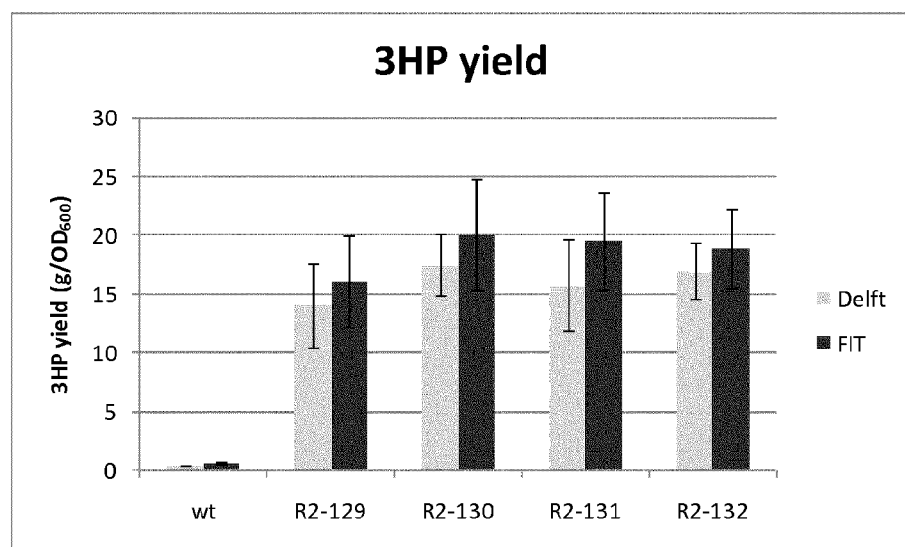
FIG. 5 shows 3HP titers and yields in strains having 3HP pathway genes in combination with or without having overexpressed native or mutant SFA1 genes, as found in Example 4.

To test the influence of 3HP tolerance gene on 3HP production, three versions of the SFA1 gene (native and two alleles) were overexpressed in the 3HP high producer (ST637) strain and characterized for 3HP production. The resulting strains and 3HP production are shown in Table 6 and FIG. 5. The 3HP titers and yields were similar to the or better than the reference strain (R2-129), showing that they were compatible and even advantageous for the production of 3HP via malonyl-CoA pathway.

The *S. cerevisiae*-3HP high producer strain has been engineered to carry several genetic modifications. Extra copies of the native acetyl-CoA synthetase (ACSse; SEQ ID NO 6), aldehyde dehydrogenase (ALD6; SEQ ID NO 7), indolepyruvate decarboxylase (PDC1; SEQ ID NO 8) and acetyl-CoA carboxylase (ACC1; SEQ ID NO 9) were introduced into the CEN.PK102-5B strain to improve the supply of precursor and redox co-factor. These genes were integrated into the genome and were under the control of either PTEF1 (SEQ ID NO 4) or PPGK1 (SEQ ID NO 5) promoters. Furthermore, the malonyl-CoA reductase gene from *Chloroflexus aurantiacus* (CaMCR; SEQ ID NO 10) responsible for converting malonyl-CoA into 3HP was also introduced into this strain.

The plasmids conferring 3HP tolerance were transformed into 3HP high producer strain the lithium acetate transformation protocol. The cells were selected on SC-Leu. For the control experiments, the strains were transformed with an empty plasmid pESC-LEU.

Six single colonies originating from four independent transformants were inoculated in 0.5 mL SC-Ura-His-Leu in 96-deep well microtiter plate with air-penetrable lid (EnzyScreen). The plates were incubated at 30° C. with 250 rpm agitation at 5 cm orbit cast overnight. 50 µL of the overnight cultures were used to inoculate 0.5 mL Delft or Feed-In-Time (FIT) Fed-batch medium (m2p-labs GmBH) in 96-deep well plate. Cultivation was carried out for 72 hours at the same conditions as above.

At the end of the cultivation the OD$_{600}$ was measured. The cultivation was diluted 20 times in a total volume of 200 µL and absorbance was measured at 600 nm wavelength on spectrophotometer (Synergy™ MX Microplate reader, BioTek).

The culture broth was spun down and the supernatant analyzed for 3HP concentration using enzymatic assay (Table 5). Enzymatic assay was carried out as following. 20

µL of standards (3HP at concentrations from 0.03 to 2 g/L in Delft medium) and samples were added to 96-well flat bottom transparent plate (Greiner). 180 µl of mix (14.8 mL water, 2 mL buffer (1 mM Tris, 25 mM $MgCl_2$, pH 8.8), 1 mL NADP+ solution (50 mg/mL), and 0.2 mL purified YdfG enzyme in PBS buffer (1500 µg/mL)) was added per well using multichannel pipet. The start absorbance at 340 nm was measured; the plate was sealed and incubated at 30° C. for 1.5 hours. After that the end absorbance at 340 nm was measured again. The difference between the end and the start values corrected for the background were in linear correlation with 3HP concentrations. The concentration of 3HP in the samples was calculated from the standard curve.

Example 5. The Proposed 3HP Detoxification Pathway

Figure 6:
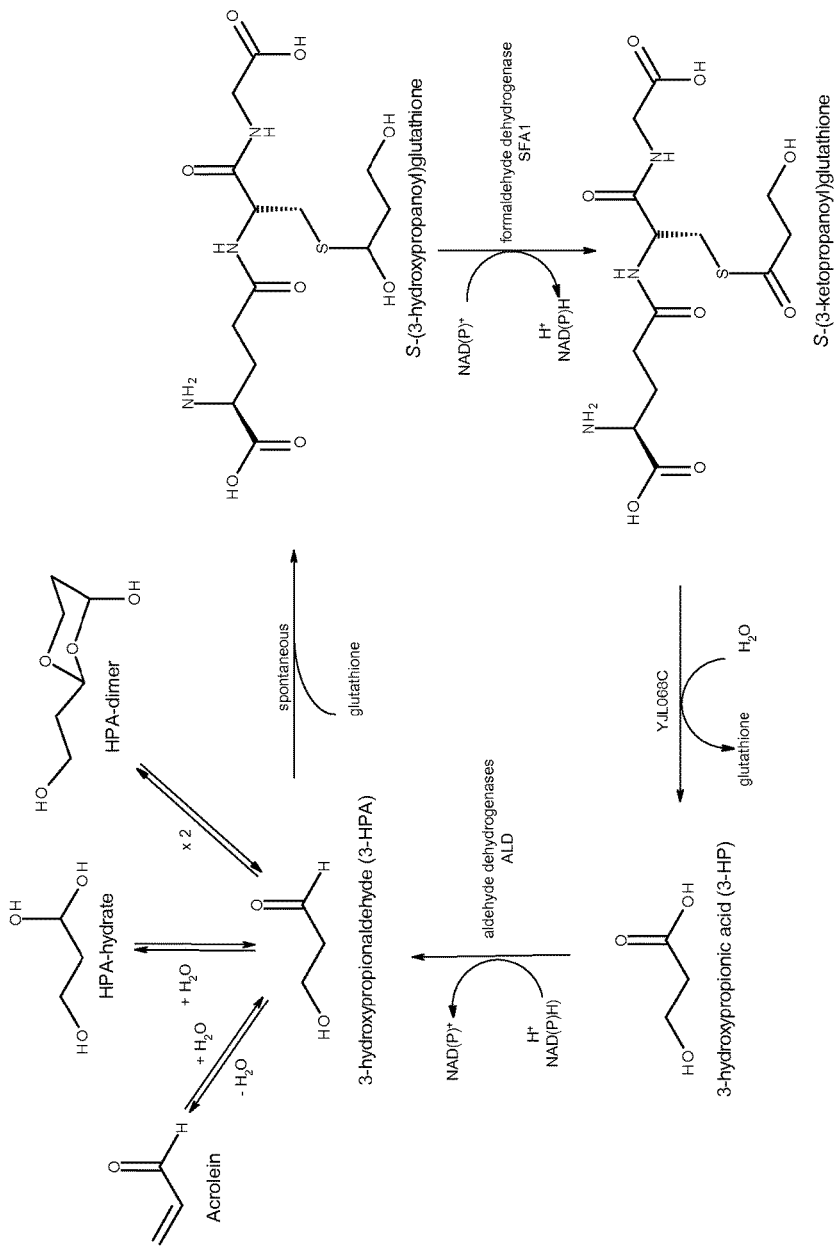
FIG. 6 shows the proposed 3HP detoxification pathway in *S. cerevisiae*.

The proposed function of SFA1 protein (Sfa1p) in formaldehyde detoxification pathway has been reported (Yasokawa et al., 2010). Formaldehyde is spontaneously reacted with intracellular glutathione (GSH) to form S-hydroxymethylglutathione which is then converted into S-formylglutathione by the Sfa1p and required $NAD(P)^+$ as a cofactor. We proposed that 3HP detoxification by the SFA1p might be similar to that observed in formaldehyde detoxification and GSH might also be involved in this process. The proposed 3HP detoxification pathway is shown in FIG. 6.

In vivo S. cerevisiae strain can convert 3HP into 3-hydroxypropionaldehyde (3HPA) by the aldehyde dehydrogenases (ALDs). As 3HPA is much more toxic than 3HP, yeast cells must efficiently eliminate this lethal compound by converting it into other less toxic compounds. 3HPA can spontaneously bind to glutathione to form S-(3-hydroxypropanoyl)glutathione which is then oxidized into S-(3-ketopropanoyl)glutathione by the Sfa1p and used $NAD(P)^+$ as a cofactor. Finally, the intermediate compound is hydrolyzed back into 3HP and released glutathione by the S-formylglutathione hydrolase encoded by Yjl068C. The proposed glutathione-dependent cyclic mechanism of 3HP detoxification has provided new insights into molecular response to 3HP in S. cerevisiae.

Example 6. The Role of GSH in 3HP Detoxification Pathway

Figure 7:
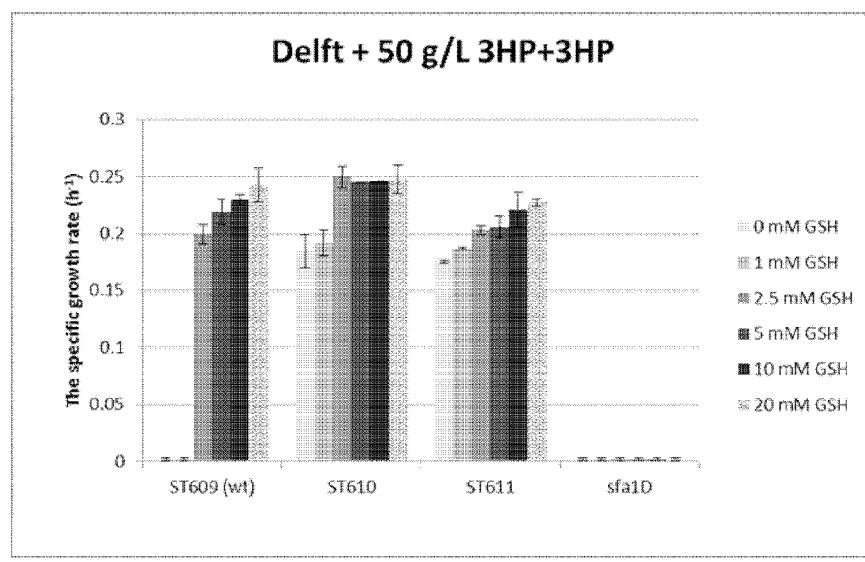
FIG. 7 shows the effect of GSH on the growth of strains of *S. cerevisiae* having the native or mutated SFA1 gene as well as the sfa1Δ strains grown on minimal medium containing 50 g/L 3HP, as described in Example 5.

The role of GSH in 3HP detoxification was investigated. The WT, SFA1-allles, and sfa1Δ strains were grown in the minimal medium with or without 50 g/L 3HP and supplemented with various concentration of external GSH (0-30 mM) and tested for 3HP tolerance. As seen in FIG. 7, GSH addition (≥2.5 mM) restored the growth of the WT S. cerevisiae in the presence of 50 g/L 3HP up to the level slightly higher than that of the SFA1-alleles strains grown without GSH supplement. Furthermore, GSH addition has also improved the growth rate of the strain carrying the SFA1 alleles. The growth of the sfa1Δ strain could not be restored by addition of GSH, further supporting the proposed role of GSH in 3HP detoxification. In addition, GSH has no significant effect on all strains grown in the minimal medium without 50 g/L 3HP.

For testing 3HP tolerance phenotype, the pre-cultures were prepared by inoculation of a single colony in 1 mL Delft buffered (pH 3.5) media containing 10 g/L 3HP. The cultures were incubated at 30° C. with 250 rpm overnight. Five µL of the overnight cultures were used to inoculate 100 µL Delft buffered (pH 3.5) with or without 50 g/L 3HP and various concentration of GSH (0, 1, 2.5, 5, 10, and 20 mM) in 96-well flat bottom plate. The 96-well plate was incubated at 30° C. with shaking in the Synergy™ MX microplate reader (BioTek) and the absorbance was measured at 600 nm wavelength every 15 min for 42 hours. Experiments were done in triplicates.

Example 7. Enhanced 3HP Tolerance in S. cerevisiae by Improving Glutathione Production (Prophetic)

From the previous example, addition of GSH enabled the viability the WT strain and improved the growth of the SFA1 allele's strains. However, the GSH addition is not economically suitable for industrial production of 3HP. Therefore, increasing intracellular pool of GSH by overexpression of genes involved in glutathione biosynthesis would be an alternative approach to reduce production cost.

In S. cerevisiae, GSH is synthesized by two consecutive ATP-dependent reactions. The γ-glutamyl-cysteine (γ-GC) synthetase (GCS, EC 6.3.2.2) encoded by GSH1 catalyzes the conjugation of L-glutamic acid and L-cysteine into γ-GC. The glutathione synthetase (GS, EC 6.3.2.3) encoded by GSH2 (SEQ ID 12) catalyzes the synthesis of GSH from γ-GC and glycine (Grant et al., 1997).

As the glutathione production requires three amino acid substrates (L-cysteine, L-glutamic acid and glycine), increasing the intracellular concentration of the substrates e.g. L-cysteine should improve the glutathione productivity. In this study, two genes in the cysteine biosynthetic pathway, MET14 and MET16, were overexpressed in combination with GSH1 and GSH2 genes and the constructed strains were tested for the effect of excess intracellular GSH concentration on 3HP tolerance.

To construct the expression vector for glutathione production, the fragments carrying the GSH1 (SEQ ID NO 11) and GSH2 (SEQ ID NO 12) genes, and the PTEF1-PPGK1 double promoter fragment (SEQ ID NO 13) containing the correct overhangs for USER cloning were generated by PCR amplification using primers and templates as indicated in Table 2. The three fragments were then ligated into pESC-URA-USER by USER cloning as previously described in example 3 to generate pESC-URA-GSH1-GSH2 plasmid.

To construct the expression vector for improving cysteine production, the fragments carrying the MET14 (SEQ ID NO14) and MET16 (SEQ ID NO15) genes containing the correct overhangs for USER cloning were generated by PCR amplification using primers and templates as indicated in Table 2. The final plasmid pESC-HIS-MET14-MET16 was constructed by ligation of MET14, MET16 and PTEF1-PPGK1 fragments into pESC-HIS-USER by USER cloning as previously described in Example 3.

The pESC-URA-GSH1-GSH2 plasmid was co-transformed with either pESC-HIS or pESC-HIS-MET14-MET16 plasmids into different background strains (ST726, ST727, and ST728) using the lithium acetate transformation protocol. The cells were selected on SC-Ura-His-Leu media. The transformants were streak purified on SC-Ura-His-Leu plate in order to obtain single colonies.

The resulting strains were tested for 3HP tolerance phenotype as described in Example 2.

Example 8. Identification of Point Mutations in the Sfa1p Protein that Confers 3HP Tolerance Phenotype The two mutations at Cys276 and Met283 residues in the Sfa1p (previously mentioned in Example 2) were investigated whether substitution of these amino acid residues with other amino acids apart from serine (Ser) and isoleucine (Ile), respectively, will also result in 3HP tolerance phenotype. Furthermore, the cysteine residues (Cys205, Cys237, and Cys290) in the Sfa1p were also selected for site-directed mutatgenesis and tested whether mutation in these residues will also improve 3HP tolerance in *S. cerevisiae*. Initial results have not shown improvement by mutation at these sites. Thus, substitution of amino acids Cys205, Cys237 and Cys290 in the Sfa1p by Ser205, Ser237, and Ser290, respectively, did not result in 3HP tolerance phenotype in *S. cerevisiae*.

Figure 8:
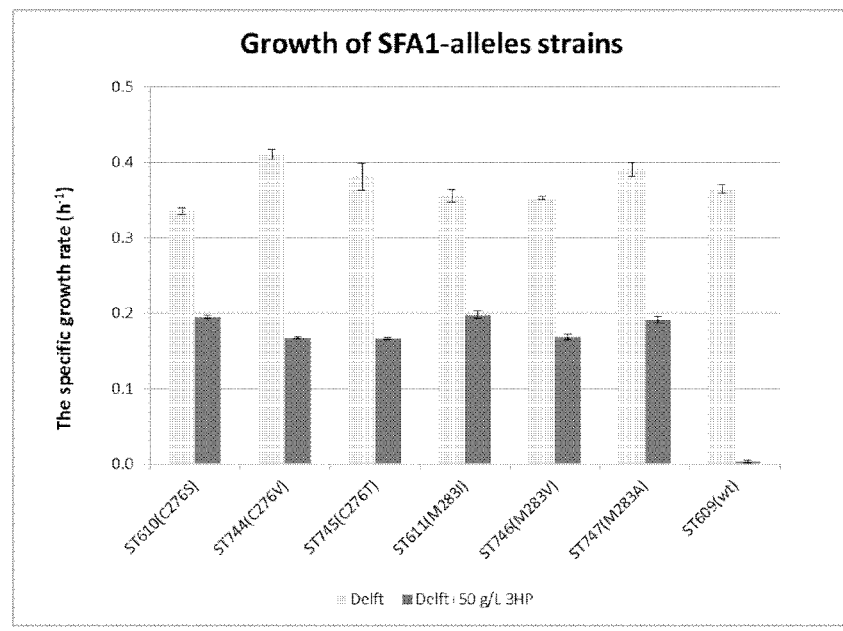
FIG. 8 shows the growth of SFA1-alleles replacement strains grown on minimal medium containing 50 g/L 3HP, as described in Example 8.

Substitution of the Cys276 residue with other amino acids e.g. threonine (Thr), glycine (Gly), valine (Val) and alanine (Ala) also gives 3HP tolerance phenotype in *S. cerevisiae*. In addition, the constructed strains where the Met283 residue in the Sfa1p was replaced with either Val or Ala also were also able to grow in the presence of 50 g/L 3HP. The growth of the resulting strains on minimal medium containing 50 g/L 3HP was shown in FIG. 8.

The PCR site-directed mutagenesis was performed to replace the Cys276 residue with either Gly, Ala, Val or Thr using primers and templates as listed in Table 2. The Met283 was changed into either Val or Ala, whereas the Cys205, Cy237 and Cys290 residues were also substituted with Ser residue (Table 2). The PCR mix contained: 30 µl water, 10 µl high fidelity Phusion® polymerase buffer (5×), 2.5 µl 10 mM dNTP, 1 µl Phusion® polymerase, 1.5 µl forward primer at 10 µM concentration, 1.5 µl reverse primer at 10 µM concentration, 1.5 µl DNA template (200 ng), and 1.5 µl DMSO (100%). The cycling program was: 98° C. for 2 min, 18 cycles of [98° C. for 10 sec, 55° C. for 30 sec, 68° C. for 9 min], 68° C. for 12 min, pause at 10° C. The PCR reaction was treated with 1 µl DpnI enzyme and incubated at 37° C. for 1 hour to remove the plasmid template. The treated PCR samples were transformed into chemically competent *E. coli* DH5alpha and selected on LB containing 100 µg/mL ampicillin. The plasmids were isolated from each *E. coli* transformants and the correct mutations in the SFA1 gene were confirmed by sequencing using primer SFA1_U1_rv.

To generate the substrates for SFA1 allele replacement, the upstream fragment for each SFA1 mutations was generated by fusion PCR using the SFA1-UP fragment, SFA1-allele fragment and the first 2/3 KlLEU2 fragment as templates and using primers KO_sfa1_fw and NB335KlLEURev1 (Table 2).

The strains carrying the point mutation in the SFA1 gene were constructed by replacing the KanMX cassette in the sfa1Δ strain with the corresponding upstream fragment (Table 2) and downstream fragment (LEU2_U_2/3_END_SFA1_DOWN fragments) of the SFA1 gene as previously mentioned in Example 3. The strains were selected on SC-Leu media. The transformants were streaked purified on SC-Leu to obtain single colonies. The correct transformants were confirmed by PCR analysis using primers KO_sfa1_test_fw and SFA1_U1-rv and the mutation in the SFA1 gene was verified by sequencing using primer SFA1_U1_rv.

The constructed strains were tested for 3HP tolerance phenotype as described in Example 3.

Example 9. Improving 3HP Tolerance in Other Cells

Based on the above examples, 3HP tolerance in *S. cerevisiae* is improved by increasing the availability of intracellular GSH either by addition of external GSH or improving GSH production. This example demonstrates that the GSH addition also helps to improve 3HP tolerance on other microorganisms e.g. *E. coli* and several yeast strains (*Schizosaccharomyces pombe, Saccharomyces kluyveri, Kluyveromyces lactis, Kluyveromyces marxianus, Yarrowia lipolytica, Cyberlindnera jadinii, Torulaspora delbrueckii, Rhodotorula minuta*).

Figure 9:
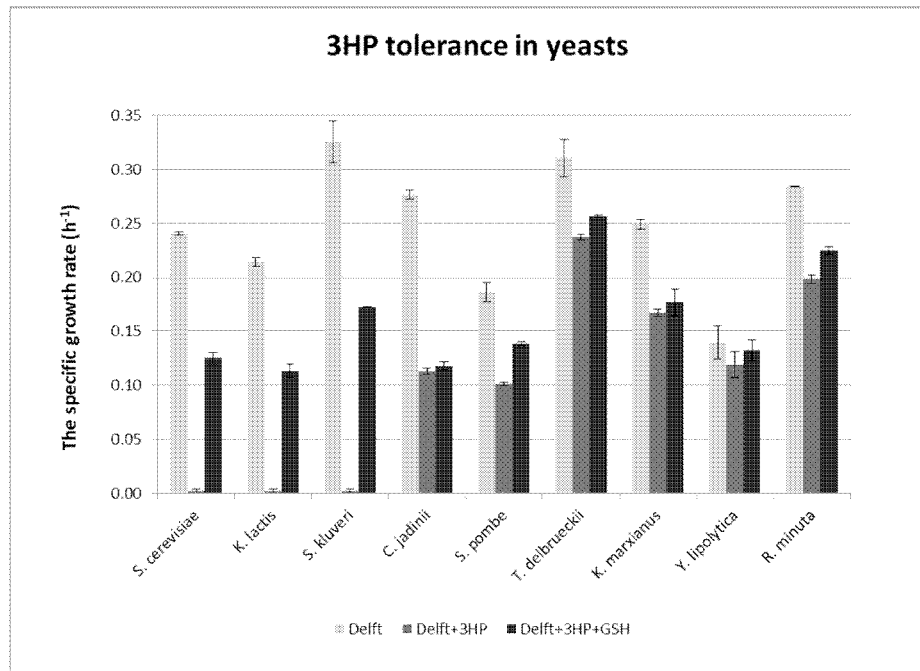
FIG. 9 shows the effect of GSH addition on the growth of several yeast strains grown on minimal medium containing 50 g/L 3HP, as described in Example 9.

As seen in FIG. 9, addition of 5 mM GSH restored the viability of several yeast strains i.e. *S. cerevisiae, S. kluyveri* and *K. lactis* grown in the presence of 50 g/L 3HP. For some yeast strains e.g. *K. marxianus, Y. lipolytica, C. jadinii, S. pombe, T. delbrueckii* and *Rhodotorula minuta*, these strains could tolerate more than 50 g/L 3HP with decreasing in the specific growth rate compared to the cells grown without the presence of 50 g/L 3HP. However, the specific growth rate of these strains grown in the presence of 50 g/L 3HP was improved by the addition of 5 mM GSH in the cultivation medium.

Figure 10:
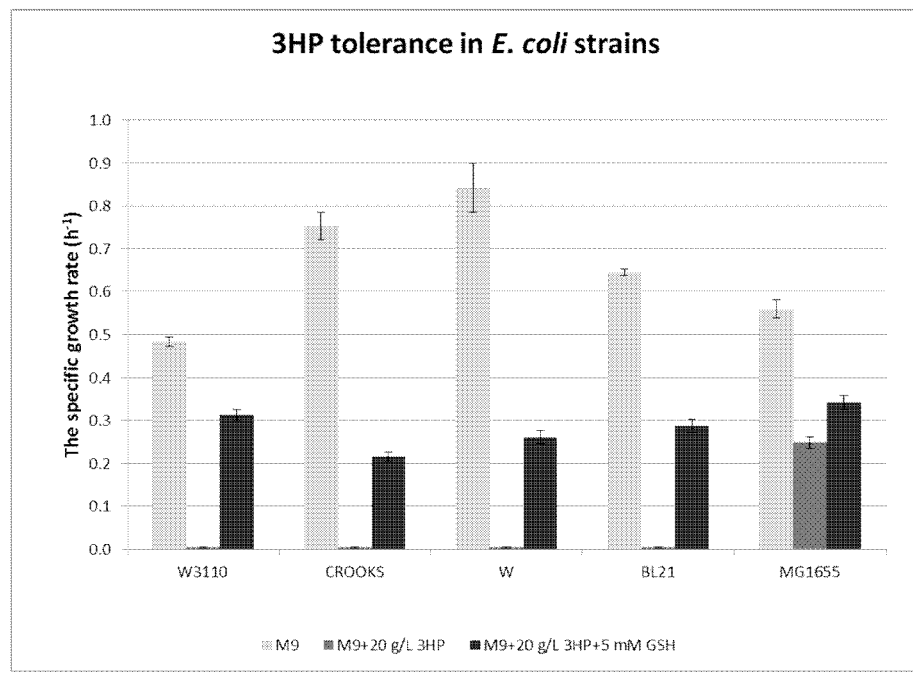
FIG. 10 shows the effect of GSH addition on the growth of several *E. coli* strains grown on M9 containing 20 g/L 3HP, as described in Example 9.

In FIG. 10, addition of 5 mM GSH also restored the viability of four *E. coli* strains i.e. W3110, CROOKS, W and BL21 grown in M9 minimal medium supplemented with 20 g/L 3HP. For MG1655, the strain could grow in M9 medium containing 20 g/L 3HP with 2.2-fold decrease in the specific growth rate compared to the cells grown in M9 medium. However, the specific growth rate of MG1655 strain was improved by the addition of 5 mM GSH in the cultivation medium containing 20 g/L 3HP.

The results strongly supported that the proposed role of GSH in 3HP detoxification mechanism are similar in several microorganisms.

The yeast strains were grown in 3 mL Delft medium (pH 6.0) at 250 rpm, 25° C., overnight. Three µL of the overnight cultures were used to inoculate 100 µL Delft medium (pH 6.0) with or without 50 g/L 3HP in 96-well flat bottom plate. The 96-well plate was incubated with shaking in the Synergy™ MX microplate reader (BioTek) at 25° C. and the absorbance was measured at 600 nm wavelength every 15 min for 72 hours. Experiments were done in triplicates, and the specific growth rate ($h^{-1}$) was calculated. The effect of GSH addition was performed by adding 5 mM GSH into the cultivation medium containing 50 g/L 3HP. The growth of each strain was determined as mentioned above.

For *E. coli*, the effect of GSH addition on the growth of *E. coli* in the presence of 20 g/L 3HP was investigated. Five platform *E. coli* wild-type strains e.g. W3110, CROOKS, W, BL21 (DE3) and MG1655 were selected for 3HP tolerance experiment. Single colony from each strain was inoculated into 3 mL M9 medium and incubated at 250 rpm, 37° C., overnight. Two µL of the overnight cultures were used to inoculate 150 µL M9 medium, M9 with 20 g/L 3HP, and M9 with 20 g/L 3HP and 5 mM GSH in 96-well flat bottom plate. The pH of all *E. coli* tested media was at pH 7.0. The 96-well plate was incubated with shaking in the ELx808™ Absorbance microplate reader (BioTek) at 37° C. and the absorbance was measured at 630 nm wavelength every 5 min for 22 hours. Experiments were done in triplicates, and the specific growth rate ($h^{-1}$) was calculated.

The composition of M9 medium was as follows: 2.0 g/L glucose, 6.8 g/L Na HPO$_4$, 3.0 g/L KH$_2$PO$_4$, 0.5 g/L NaCl, 1.0 g/L NH$_4$Cl, 0.24 g/L MgSO$_4$, 0.011 g/L CaCl$_2$, 0.5 mL/L trace elements solution, and 1.0 mL/L Wolfe's Vitamin solution. The trace elements solution included 1.0 g/L FeCl$_3$.6H$_2$O, 0.18 g/L ZnSo$_4$.7H$_2$O, 0.12 g/L CuCl$_2$.2H$_2$O, 0.12 g/L MnSO$_4$.H$_2$O, and 0.18 g/L CoCl$_2$.6H$_2$O. The Wolfe's vitamin solution included 10 mg/L pyridoxine hydrochloride, 5.0 mg/L thiamine HCl, 5.0 mg/L riboflavin, 5.0 mg/L nicotinic acid, 5.0 mg/L calcium-(+) phantothenate, 5.0 mg/L para-amino benzoic acid, 5.0 mg/L thiotic acid, 2.0 mg/L d-biotin, 2.0 mg/L folic acid, and 0.1 mg/L vitamin B12. The trace elements and vitamin solutions were sterile-filtered and the solution was stored at 4° C. The M9 salt solution was prepared as a 10× concentrate solution and sterilized by autoclaving. 20% Glucose solution, 1M MgSO$_4$, and 1M CaCl$_2$ stock solutions were autoclaved separately.

REFERENCES

Erdeniz, N., Mortensen, U. H., and Rothstein, R. Cloning-free PCR-based allele replacement methods. (1997) *Genome Res* 7: 1174-1183.

Fernández, M. R., Biosca, J. A., Torres, D., Crosas, B., and Parés, X. A double residue substitution in the coenzyme-binding site accounts for the different kinetic properties between yeast and human formaldehyde dehydrogenases. (1999) *J Biol Chem* 274(53): 37869-37875.

Gietz, R. D. and Woods, R. A. Transformation of yeast by lithium acetate/single-stranded carrier DNA/polyethylene glycol method. (2002) *Methods Enzymol* 350:87-96

Grant, C. M., MacIver, F. H., and Dawes, I. W. Glutathione synthetase is dispensable for growth under both normal and oxidative stress conditions in the yeast *Saccharomyces cervisiae* due to an accumulation of the dipeptide gamma-glutamylcysteine. (1997) *Mol Biol Cell* 8:1699-1707.

Hügler, M., Meenedez, C, Schägger, H., and Fuchs, G. Malonyl-Coenzyme A Reductase from *Chloroflexus Aurantiacus*, a Key Enzyme of the 3-Hydroxypropionate Cycle for Autotrophic CO2 Fixation. (2002) *J Bacteriol* 184(9):2404-2410.

Kwak S., Park, Y. C, and Seo, J. H. Biosynthesis of 3-hydroxypropionic Acid from Glycerol in Recombinant *Escherichia coli* Expressing *Lactobacillus brevis* dhaB and dhaR Gene Clusters and *E. coli* K-12 aldH. (2013) *Bioresour Technol* 135: 432-439.

Luo, L. H., Kim, C. H., Heo, S. Y., Oh, B. R., Hong, W. K., Kin, S., Kim, D. H. and Seo, J. W. Production of 3-hydroxypropionic Acid Through Propionaldehyde Dehydrogenase PduP Mediated Biosynthetic Pathway in *Klebsiella pneumoniae*. (2012) *Bioresour Technol* 103(1): 1-6.

Luo, L. H., Seo, J. W., Oh, B. R., Seo, P. S., Heo, S. Y., Hong, W. K., Kim, D. H. and Kim, C. H. Stimulation of Reductive Glycerol Metabolism by Overexpression of an Aldehyde Dehydrogenase in a Recombinant *Klebsiella pneumoniae* Strain Defective in the Oxidative Pathway. (2011). *J Ind Microbiol Biotechnol* 38(8): 991-999.

Molin and Blomberg, Dihydroxyacetone detoxification in *Saccharomyces cerevisiae* involves formaldehyde dissimilation. (2006) *Mol Microbiol* 60(4), 925-938.

Rathnasingh, C., Raj, S. M., Jo, J. E., and Park, S. Development and Evaluation of Efficient Recombinant *Escherichia coli* Strains for the Production of 3-hydroxypropionic Acid from Glycerol. (2009) *Biotechnol Bioeng* 104(4): 729-739.

Wen, S., Zhang, T. and Tan, T. Utilization of amino acids to enhance glutathione production in *Saccharomyces cerevisiae*. (2004) *Enzyme Microbial Tech* 35: 501-507.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention may be summarised according to the following clauses:

1. A cell having a metabolic pathway producing 3-hydroxypropionic acid (3HP), said cell exhibiting tolerance for 3HP and having one or more genetic modifications that provide for an enhanced activity of 3HP detoxification by a reaction pathway that includes a glutathione-dependent dehydrogenase reaction.
2. A cell as defined in clause 1, wherein a said genetic modification is one or more mutations in a gene encoding a glutathione-dependent formaldehyde dehydrogenase conferring said tolerance.
3. A cell as defined in clause 2, wherein said one or more mutations are in a gene equivalent to SFA1 of *Saccharomyces cerevisiae*.
4. A cell as defined in clause 3, wherein said one or more mutations are in a gene encoding a protein having the sequence SEQ ID NO 1 or a protein with more than 80% homology to SEQ ID NO 1.
5. A cell as defined in any one of clauses 2 to 4, wherein the mutation is at a position equivalent to the position aa276 Cys and/or at aa283 Met of the SFA1 gene of *Saccharomyces cerevisiae*.
6. A cell as defined in clause 5, wherein said mutation in gene SFA1 is Cys276→Ser, Cys276→Val, Cys276→Thr, Cys276→Gly, Cys276→Ala and/or Met283→Ile, Met283→Ala, Met283→Val.
7. A cell as defined in any preceding clause, wherein a said genetic modification produces overexpression of a native, or heterologous, or mutated glutathione-dependent formaldehyde dehydrogenase to confer said 3HP tolerance.
8. A cell as defined in clause 7, wherein said genetic modification produces overexpression of a native or heterologous glutathione-dependent formaldehyde dehydrogenase which has the sequence SEQ ID NO 1 or is a protein with more than 80% homology to SEQ ID NO 1.
9. A cell as defined in any preceding clause, wherein the cell is genetically modified for increased production of glutathione.
10. A cell as defined in clause 9, wherein the cell overexpresses the glutathione biosynthetic genes gamma-glutamylcysteine synthetase and glutathione synthetase.
11. A cell as defined in clause 9 or clause 10, wherein the cell overexpresses genes that enhance the production of amino acid precursors for glutathione biosynthesis.
12. A cell as defined in any preceding clause, wherein said metabolic pathway comprises the enzyme malonyl-CoA reductase and/or the enzyme malonyl-CoA reductase (malonate semialdehyde-forming) in combination with the enzyme 3-hydroxyisobutyrate dehydrogenase and/or the enzyme hydroxypropionate dehydrogenase.
13. A cell as defined in any one of clauses 1 to 11, wherein said metabolic pathway comprises a malonyl-CoA reductase gene and an acetyl-CoA carboxylase gene.
14. A cell as defined in clause 13, wherein said metabolic pathway comprises the malonyl-CoA reductase gene from *Chloroflexus aurantiacus* (CaMCR).
15. A cell as defined in clause 14, wherein said metabolic pathway comprises the malonyl-CoA reductase gene from *Chloroflexus aurantiacus* (CaMCR) and the acetyl-CoA carboxylase gene (ACC1) of *S. cerevisiae*.

16. A cell as defined in any one of clauses 1 to 11, wherein said metabolic pathway comprises beta-alanine pyruvate aminotransferase and/or gamma-aminobutyrate transaminase in combination with hydroxyisobutyrate dehydrogenase and/or hydroxypropionate dehydrogenase.

17. A cell as defined in clause 16, wherein said metabolic pathway comprises the beta-alanine pyruvate aminotransferase from *Bacillus cereus* together with one of the following: 3-hydroxypropanoate dehydrogenase from *Metallosphaera sedula*, 3-hydroxypropanoate dehydrogenase from *Sulfolobus tokadaii*, 3-hydroxypropanoate dehydrogenase from *E. coli* (YdfGp), 3-hydroxypropanoate dehydrogenase from *E. coli* (RutEp), 3-hydroxyisobutyrate dehydrogenase from *Pseudomonas aeruginosa*, 3-hydroxyisobutyrate dehydrogenase from *P. putida*, 3-hydroxyisobutyrate dehydrogenase from *Bacillus cereus*, or 3-hydroxyisobutyrate dehydrogenase from *Candida albicans*.

18. A cell as defined in any one of clauses 1 to 11, wherein said metabolic pathway comprises glycerol dehydratase and alcohol dehydrogenase.

19. A cell as defined in any one of clauses 1 to 11, wherein said metabolic pathway comprises lactate dehydrogenase, propionate CoA-transferase, lactoyl-CoA dehydratase, enoyl-CoA hydratase and 3-hydroxyisobutyryl-CoA hydrolase.

20. A cell as defined in any preceding clause, wherein said cell is a yeast cell.

21. A cell as defined in clause 18, wherein the yeast cell is of the genus *Saccharomyces, Schizosaccharomyces, Kluyveromyces, Pichia, Candida, Yarrowia, Brettanomyces, Hansenula, Lipomyces*, and *Issatchenkia*.

22. A cell as defined in clause 18, wherein the yeast cell is a *Saccharomyces cerevisiae* cell.

23. A cell as defined in clause 22, wherein said genetic modification comprises one or more mutations in gene SFA1 at aa276 Cys and/or at aa283 Met.

24. A cell as defined in any one of clauses 1 to 19, wherein said cell is a bacterial cell.

25. A cell as defined in any one of clauses 1 to 19, wherein said bacterial cell is of the genus *Eschericia, Lactobacillus, Lactococcus, Corynebacterium, Clostridium*, or *Bacillus*.

26. A cell as defined in any one of clauses 20 to 25, wherein the cell is *S. cerevisiae, S. pombe, S. kluyveri, K. lactis, K. marxianus, Y. lipolytica, T. delbreueckii, R. minuta, I. orientalis, P. stipites, L. starkeyi, C. guilliermondii*, or *E. coli*.

27. A yeast exhibiting tolerance for 3HP, said yeast having a mutation in gene SFA1 conferring said tolerance.

28. A yeast as defined in clause 27, wherein the yeast is *Saccharomyces cerevisiae* and said mutation in gene SFA1 is at aa276 Cys and/or at aa283 Met.

29. A yeast as defined in clause 28, wherein said mutation in gene SFA1 is Cys276→Ser, Cys276→Val, Cys276→Thr, Cys276→Gly, Cys276→Ala and/or Met276→Ile, Met276→Ala, Met276→Val 30. A yeast as defined in clause 29, wherein said mutation in gene SFA1 is Cys→Ser(aa276) and/or Met→Ile (aa283).

31. A method of producing 3HP comprising cultivating a 3HP producing cell under 3HP producing conditions in a culture medium so as to produce 3HP, wherein toxicity of 3HP is reduced by an enhanced activity of 3HP detoxification by a reaction pathway that includes a glutathione-dependent dehydrogenase reaction.

32. A method as defined in clause 31, wherein said culture medium is supplemented with glutathione.

33. A method as defined in clause 32, wherein glutathione is added to the culture medium to produce a concentration therein of >2.5 mM.

34. A method as defined in clause 31 or clause 32, wherein said cell has a genetic modification conferring an enhanced glutathione production ability thereon.

35. A method as defined in clause 34, wherein the cell overexpresses the glutathione biosynthetic genes gamma-glutamylcysteine synthetase and glutathione synthetase.

36. A method as defined in clause 34 or clause 35, wherein the cell overexpresses genes that enhance the production of amino acid precursors for glutathione biosynthesis.

37. A method as defined in any one of clauses 31 to 36, wherein a concentration of 3HP in excess of 1 g/l is produced in said culture medium.

38. The use of an enhanced glutathione-dependent dehydrogenase reaction in a cell to enhance tolerance of said cell to 3HP.

39. A use as defined in clause 38, wherein said reaction is one converting S-(3-hydroxypropanoyl)glutathione to S-(3-ketopropanoyl)glutathione.

The invention claimed is:

1. A cell having a metabolic pathway producing 3-hydroxypropionic acid (3HP), said cell exhibiting tolerance for 3HP and having one or more genetic modifications that provide for an enhanced activity of 3HP detoxification by a reaction pathway that includes a glutathione-dependent dehydrogenase reaction, wherein said one or more genetic modifications comprises one or more mutations in a gene' encoding a glutathione-dependent formaldehyde dehydrogenase conferring tolerance for 3HP, and wherein the one or more mutations is at a position equivalent to the position aa276 Cys and/or at aa283 Met of the SFA1 gene of *Saccharomyces cerevisiae*.

2. A cell as claimed in claim 1, wherein said one or more mutations are in a gene encoding a protein having the sequence SEQ ID NO 1 or a protein with more than 80% homology to SEQ ID NO 1.

3. A cell as claimed in claim 1, wherein said mutation in gene SFA1 is Cys276→Ser, Cys276→Val, Cys276→Thr, Cys276→Gly, Cys276→Ala and/or Met283→Ile, Met283→Ala, Met283→Val.

4. A cell as claimed in claim 1, wherein a said genetic modification produces overexpression of a native, or heterologous, or mutated glutathione-dependent formaldehyde dehydrogenase to confer said 3HP tolerance.

5. A cell as claimed in claim 1, wherein the cell is genetically modified for increased production of glutathione.

6. A cell as claimed in claim 5, wherein the cell overexpresses genes that enhance the production of amino acid precursors for glutathione biosynthesis.

7. A cell as claimed in claim 1, wherein said metabolic pathway comprises the enzyme malonyl-CoA reductase and/or the enzyme malonyl-CoA reductase (malonate semialdehyde-forming) in combination with the enzyme 3-hydroxyisobutyrate dehydrogenase and/or the enzyme hydroxypropionate dehydrogenase, or wherein said metabolic pathway comprises a malonyl-CoA reductase gene and an acetyl-CoA carboxylase gene, or wherein said metabolic pathway comprises beta-alanine pyruvate aminotransferase and/or gamma-aminobutyrate transaminase in combination with hydroxyisobutyrate dehydrogenase and/or hydroxypropionate dehydrogenase or wherein said metabolic pathway comprises glycerol dehydratase and alcohol dehydrogenase or wherein said metabolic pathway comprises lactate dehydrogenase, propionate CoA-transferase, lactoyl-CoA dehydratase, enoyl-CoA hydratase and 3-hydroxyisobutyryl-CoA hydrolase.

8. A cell as claimed in claim 1, wherein said cell is a yeast cell or is a bacterial cell.

9. A method of producing 3HP comprising cultivating a 3HP producing cell under 3HP producing conditions in a culture medium so as to produce 3HP, wherein toxicity of 3HP is reduced by an enhanced activity of 3HP detoxification by a reaction pathway that includes a glutathione-dependent dehydrogenase reaction, and wherein said culture medium is supplemented with glutathione.

10. A method of producing 3HP comprising cultivating a 3HP producing cell under 3HP producing conditions in a culture medium so as to produce 3HP, wherein toxicity of 3HP is reduced by an enhanced activity of 3HP detoxification by a reaction pathway that includes a glutathione-dependent dehydrogenase reaction, and wherein the cell overexpresses the glutathione biosynthetic genes gamma-glutamylcysteine synthetase and glutathione synthetase.

11. A method as claimed in any one of claim 9, wherein the cell overexpresses genes that enhance the production of amino acid precursors for glutathione biosynthesis.

* * * * *

SEQUENCE LISTING

```
<160> NUMBER OF SEQ ID NOS: 57

<210> SEQ ID NO 1
<211> LENGTH: 1161
<212> TYPE: DNA
<213> ORGANISM: Saccharomyces cerevisiae
<220> FEATURE:
<221> NAME/KEY: source
<222> LOCATION: 1..1161
<223> OTHER INFORMATION: /mol_type="unassigned DNA"
      /organism="Saccharomyces cerevisiae"

<400> SEQUENCE: 1
atgtccgccg ctactgttgg taaacctatt aagtgcattg ctgctgttgc gtatgatgcg      60
aagaaaccat taagtgttga agaaatcacg gtagacgccc caaaagcgca cgaagtacgt      120
```

```
atcaaaattg aatatactgc tgtatgccac actgatgcgt acactttatc aggctctgat      180
ccagaaggac ttttcccttg cgttctgggc cacgaaggag ccggtatcgt agaatctgta      240
ggcgatgatg tcataacagt taagcctggt gatcatgtta ttgctttgta cactgctgag      300
tgtggcaaat gtaagttctg tacttccggt aaaaccaact tatgtggtgc tgttagagct      360
actcaaggga aggtgtaat gcctgatggg accacaagat tcataatgc gaaaggtgaa        420 gatatatacc atttcatggg ttgctctact ttttccgaat atactgtggt ggcagatgtc      480
tctgtggttg ccatcgatcc aaaagctccc ttggatgctg cctgtttact gggttgtggt      540
gttactactg gttttggggc ggctcttaag acagctaatg tgcaaaaagg cgataccgtt      600
gcagtatttg gctgcgggac tgtaggactc tccgttatcc aaggtgcaaa gttaaggggc      660
gcttccaaga tcattgccat tgacattaac aataagaaaa aacaatattg ttctcaattt      720
ggtgccacgg attttgttaa tcccaaggaa gatttggcca agatcaaac tatcgttgaa       780 aagttaattg aaatgactga tggggtctg gattttactt ttgactgtac tggtaatacc       840
aaaattatga gagatgcttt ggaagcctgt cataaaggtt ggggtcaatc tattatcatt      900
ggtgtggctg ccgctggtga agaaatttct acaaggccgt ccagctggt cactggtaga      960 gtgtggaaag gctctgcttt tggtggcatc aaaggtagat ctgaaatggg cggtttaatt     1020
aaagactatc aaaaggtgc cttaaaagtc gaagaattta tcactcacag gagaccattc      1080
aaagaaatca atcaagcctt tgaagatttg cataacggtg attgcttaag aaccgtcttg     1140
aagtctgatg aaataaaata g                                               1161
```

<210> SEQ ID NO 2
<211> LENGTH: 1161
<212> TYPE: DNA
<213> ORGANISM: Saccharomyces cerevisiae
<220> FEATURE:
<221> NAME/KEY: source
<222> LOCATION: 1..1161
<223> OTHER INFORMATION: /mol_type="unassigned DNA"
    /organism="Saccharomyces cerevisiae"

<400> SEQUENCE: 2

```
atgtccgccg ctactgttgg taaacctatt aagtgcattg ctgctgttgc gtatgatgcg       60
aagaaaccat taagtgttga agaaatcacg gtagacgccc caaaagcgca cgaagtacgt      120
atcaaaattg aatatactgc tgtatgccac actgatgcgt acactttatc aggctctgat      180
ccagaaggac ttttcccttg cgttctgggc cacgaaggag ccggtatcgt agaatctgta      240
ggcgatgatg tcataacagt taagcctggt gatcatgtta ttgctttgta cactgctgag      300
tgtggcaaat gtaagttctg tacttccggt aaaaccaact tatgtggtgc tgttagagct      360
actcaaggga aggtgtaat gcctgatggg accacaagat tcataatgc gaaaggtgaa        420 gatatatacc atttcatggg ttgctctact ttttccgaat atactgtggt ggcagatgtc      480
tctgtggttg ccatcgatcc aaaagctccc ttggatgctg cctgtttact gggttgtggt      540
gttactactg gttttggggc ggctcttaag acagctaatg tgcaaaaagg cgataccgtt      600
gcagtatttg gctgcgggac tgtaggactc tccgttatcc aaggtgcaaa gttaaggggc      660
gcttccaaga tcattgccat tgacattaac aataagaaaa aacaatattg ttctcaattt      720
ggtgccacgg attttgttaa tcccaaggaa gatttggcca agatcaaac tatcgttgaa       780 aagttaattg aaatgactga tggggtctg gattttactt ttgactctac tggtaatacc       840
aaaattatga gagatgcttt ggaagcctgt cataaaggtt ggggtcaatc tattatcatt      900
```

```
ggtgtggctg ccgctggtga agaaatttct acaaggccgt tccagctggt cactggtaga      960
gtgtggaaag gctctgcttt tggtggcatc aaaggtagat ctgaaatggg cggtttaatt     1020
aaagactatc aaaaaggtgc cttaaaagtc gaagaattta tcactcacag gagaccattc    1080
aaagaaatca atcaagcctt tgaagatttg cataacggtg attgcttaag aaccgtcttg     1140
aagtctgatg aaataaaata g                                               1161
```

<210> SEQ ID NO 3
<211> LENGTH: 1161
<212> TYPE: DNA
<213> ORGANISM: Saccharomyces cerevisiae
<220> FEATURE:
<221> NAME/KEY: source
<222> LOCATION: 1..1161
<223> OTHER INFORMATION: /mol_type="unassigned DNA"
      /organism="Saccharomyces cerevisiae"

<400> SEQUENCE: 3

```
atgtccgccg ctactgttgg taaacctatt aagtgcattg ctgctgttgc gtatgatgcg       60
aagaaaccat taagtgttga gaaatcacg gtagacgccc caaaagcgca cgaagtacgt      120
atcaaaattg aatatactgc tgtatgccac actgatgcgt cactttatc aggctctgat      180 ccagaaggac ttttcccttg cgttctgggc cacgaaggag ccggtatcgt agaatctgta     240
ggcgatgatg tcataacagt taagcctggt gatcatgtta ttgctttgta cactgctgag     300
tgtggcaaat gtaagttctg tacttccggt aaaaccaact tatgtggtgc tgttagagct    360
actcaaggga aaggtgtaat gcctgatggg accacaagat tcataatgc gaaaggtgaa     420 gatatatacc atttcatggg ttgctctact ttttccgaat atactgtggt ggcagatgtc    480
tctgtggttg ccatcgatcc aaaagctccc ttggatgctg cctgtttact ggggttgtggt    540 gttactactg gttttgggc ggctcttaag acagctaatg tgcaaaaagg cgataccgtt    600
gcagtatttg gctgcgggac tgtaggactc tccgttatcc aaggtgcaaa gttaagggc    660 gcttccaaga tcattgccat tgacattaac aataagaaaa acaatatttg ttctcaattt     720
ggtgccacgg atttttgttaa tcccaaggaa gatttggcca aagatcaaac tatcgttgaa   780
aagttaattg aaatgactga tggggttctg gattttactt ttgactgtac tggtaatacc    840
aaaattataa gagatgcttt ggaagcctgt cataaaggtt ggggtcaatc tattatcatt     900
ggtgtggctg ccgctggtga agaaatttct acaaggccgt tccagctggt cactggtaga     960
gtgtggaaag gctctgcttt tggtggcatc aaaggtagat ctgaaatggg cggtttaatt    1020
aaagactatc aaaaaggtgc cttaaaagtc gaagaattta tcactcacag gagaccattc    1080
aaagaaatca atcaagcctt tgaagatttg cataacggtg attgcttaag aaccgtcttg     1140
aagtctgatg aaataaaata g                                              1161
```

<210> SEQ ID NO 4
<211> LENGTH: 420
<212> TYPE: DNA
<213> ORGANISM: Saccharomyces cerevisiae
<220> FEATURE:
<221> NAME/KEY: source
<222> LOCATION: 1..420
<223> OTHER INFORMATION: /mol_type="unassigned DNA"
      /organism="Saccharomyces cerevisiae"

<400> SEQUENCE: 4

```
gcacacacca tagcttcaaa atgtttctac tccttttttta ctcttccaga ttttctcgga      60
ctccgcgcat cgccgtacca cttcaaaaca cccaagcaca gcatactaaa tttcccctct    120
```

```
ttcttcctct agggtgtcgt taattacccg tactaaaggt ttggaaaaga aaaaagagac    180
cgcctcgttt cttttctct gtcgaaaaag gcaataaaaa ttttatcac gtttcttttt    240 cttgaaaatt ttttttttg attttttct ctttcgatga cctcccattg atatttaagt    300
taataaacgg tcttcaattt ctcaagtttc agtttcattt ttcttgttct attacaactt    360
tttttacttc ttgctcatta gaaagaaagc atagcaatct aatctaagtt ttaattacaa    420
```

<210> SEQ ID NO 5
<211> LENGTH: 984
<212> TYPE: DNA
<213> ORGANISM: Saccharomyces cerevisiae
<220> FEATURE:
<221> NAME/KEY: source
<222> LOCATION: 1..984
<223> OTHER INFORMATION: /mol_type="unassigned DNA"
    /organism="Saccharomyces cerevisiae"

<400> SEQUENCE: 5

```
ggaagtacct tcaaagaatg gggtcttatc ttgttttgca agtaccactg agcaggataa     60
taatagaaat gataatatac tatagtagag ataacgtcga tgacttccca tactgtaatt    120
gcttttagtt gtgtattttt agtgtgcaag tttctgtaaa tcgattaatt ttttttttctt    180 tcctcttttt attaacctta atttttattt tagattcctg acttcaactc aagacgcaca    240
gatattataa catctgcata ataggcattt gcaagaatta ctcgtgagta aggaaagagt    300
gaggaactat cgcatacctg catttaaaga tgccgatttg ggcgcgaatc ctttatttg    360 gcttcacccct catactatta tcagggccag aaaaaggaag tgtttccctc cttcttgaat    420
tgatgttacc ctcataaagc acgtggcctc ttatcgagaa agaaattacc gtcgctcgtg    480
atttgtttgc aaaaagaaca aaactgaaaa aacccagaca cgctcgactt cctgtcttcc    540
tattgattgc agcttccaat ttcgtcacac aacaaggtcc tagcgacggc tcacaggttt    600
tgtaacaagc aatcgaaggt tctggaatgg cgggaaaggg tttagtacca catgctatga    660
tgcccactgt gatctccaga gcaaagttcg ttcgatcgta ctgttactct ctctctttca    720
aacagaattg tccgaatcgt gtgacaacaa cagcctgttc tcacacactc ttttcttcta    780
accaaggggg tggtttagtt tagtagaacc tcgtgaaact tacatttaca tatatataaa    840
cttgcataaa ttggtcaatg caagaaatac atatttggtc ttttctaatt cgtagttttt    900
caagttctta gatgctttct ttttctcttt tttacagatc atcaaggaag taattatcta    960 cttttttacaa caaatataaa acaa                                          984
```

<210> SEQ ID NO 6
<211> LENGTH: 1959
<212> TYPE: DNA
<213> ORGANISM: Saccharomyces cerevisiae
<220> FEATURE:
<221> NAME/KEY: source
<222> LOCATION: 1..1959
<223> OTHER INFORMATION: /mol_type="unassigned DNA"
    /organism="Saccharomyces cerevisiae"

<400> SEQUENCE: 6

```
atgtcacaaa cacacaaaca tgctattcct gcgaatatcg ctgacaggtg cttaatcaac     60
cctgaacaat acgaaacgaa gtacaagcag tctatcaacg atcctgatac tttctggggc    120
gagcaaggta agatactcga ttggattact ccatatcaaa aggtcaaaaa cacatccttt    180
gctcctggaa atgtgtcaat caagtggtac gaggacggca ctctaaacct agctgctaat    240
```

```
tgcttggatc gacacctcca ggaaaatggt gacagaacgg caatcatttg ggaaggtgat    300
gatacttctc aatctaagca catctcctac agagagttac acagagatgt ttgcagattc    360
gcgaatactt tactggacct gggtatcaaa aagggcgatg ttgtggcaat ctacatgcct    420
atggtcccag aggcagctgt ggcaatgttg gcctgtgcca aataggagc agtccatagc     480 gttatctttg gcggattctc ccctgaagcc gttgctggga gaatcattga ctcatcaagt    540
agattagtta tcactgccga cgaaggtgtt agagcaggta gatccatccc attgaagaaa    600
aacgttgatg acgcgttgaa aaacccaaac gttacgagtg tggagcatgt aattgtacta    660
aagcgtaccg gctctgatat agactggcag gaaggtaggg atttgtggtg gagagatctt    720
attgagaaag caagtccaga acaccaacca gaagcaatga atgcggaaga tccattgttc    780
atcttgtata catctgggtc aactggcaaa ccaaaaggtg ttttgcatac aacaggtggt    840
tatctcgtat acgccgcaac aacctttaag tacgtttttg attaccatcc aggtgatatc    900
tactggtgta ccgctgatgt cggttgggtt actggtcata gttacctgct ttacggtcca    960
ctggcatgcg gcgcaaccac tttgatgttt gaaggagtac caaactggcc aaccccagcc   1020
aggatgtgtc aagtggtcga taaacaccaa gtgaacatat tgtacacagc cccaaccgcc   1080
attagagcgc taatggccga aggagataag gcgattgagg gaacagatag aagtagccta   1140
cgtatcttag gatccgttgg cgagccaatc aatccagaag cttgggaatg gtattggaaa   1200
aagattggta aggaaaagtg tccagtagtg gatacatggt ggcaaactga acaggtgga    1260 ttcatgatta cacctcttcc aggtgcaata gaattgaagg ctgggtctgc tactaggcct   1320
ttcttcggcg tccaacctgc tttagtagac aacgaagggc atccacaaga gggggcaaca   1380
gaaggcaatc tagtgataac tgattcctgg cctggtcagg ctagaacatt gtttggtgat   1440
cacgaaagat tcgaacaaac ctatttctca actttcaaaa acatgtatt cagcggtgac   1500 ggtgcgagaa gagacgaaga tgggtactac tggattaccg gcagagtaga tgacgtcctt   1560
aacgtatctg gacatcgtct gggtacagct gagattgagt cagctttagt tgctcatcct   1620
aagattgctg aagctgcagt cgttggcatc ccacacgcta tcaagggtca agccatatac   1680
gcatatgtta cactcaacca tggtgaggaa ccatctccag agctatacgc agaggtcaga   1740
aattgggttc gaaaggaaat agggccttta gccacaccag atgttttgca ttggacagat   1800
tcattgccta agacaagatc tggaaagatt atgagacgta tacttagaaa gatcgccgcc   1860
ggagatacgt ctaacttagg tgatacttct actcttgccg atccaggcgt ggtcgaaaaa   1920
cctttagagg aaaaacaagc tattgctatg ccatcatga                         1959
```

<210> SEQ ID NO 7
<211> LENGTH: 1503
<212> TYPE: DNA
<213> ORGANISM: Saccharomyces cerevisiae
<220> FEATURE:
<221> NAME/KEY: source
<222> LOCATION: 1..1503
<223> OTHER INFORMATION: /mol_type="unassigned DNA"
      /organism="Saccharomyces cerevisiae"

<400> SEQUENCE: 7

```
atgactaagc tacactttga cactgctgaa ccagtcaaga tcacacttcc aaatggtttg     60
acatacgagc aaccaaccgg tctattcatt aacaacaagt ttatgaaagc tcaagacggt    120
aagacctatc ccgtcgaaga tccttccact gaaaacaccg tttgtgaggt ctcttctgcc    180
accactgaag atgttgaata tgctatcgaa tgtgccgacc gtgctttcca cgacactgaa    240
```

```
tgggctaccc aagacccaag agaaagaggc cgtctactaa gtaagttggc tgacgaattg      300
gaaagccaaa ttgacttggt ttcttccatt gaagctttgg acaatggtaa aactttggcc      360
ttagcccgtg gggatgttac cattgcaatc aactgtctaa gagatgctgc tgcctatgcc      420
gacaaagtca acggtagaac aatcaacacc ggtgacggct acatgaactt caccacctta      480
gagccaatcg gtgtctgtgg tcaaattatt ccatggaact ttccaataat gatgttggct      540
tggaagatcg ccccagcatt ggccatgggt aacgtctgta tcttgaaacc cgctgctgtc      600
acacctttaa atgccctata ctttgcttct ttatgtaaga aggttggtat tccagctggt      660
gtcgtcaaca tcgttccagg tcctggtaga actgttggtg ctgctttgac caacgaccca      720
agaatcagaa agctggcttt taccggttct acagaagtcg gtaagagtgt tgctgtcgac      780
tcttctgaat ctaacttgaa gaaaatcact ttggaactag gtggtaagtc cgcccatttg      840
gtctttgacg atgctaacat taagaagact ttaccaaatc tagtaaacgg tattttcaag      900
aacgctggtc aaatttgttc ctctggttct agaattacg ttcaagaagg tatttacgac      960
gaactattgg ctgctttcaa ggcttacttg gaaaccgaaa tcaagttgg taatccattt      1020 gacaaggcta acttccaagg tgctatcact aaccgtcaac aattcgacac aattatgaac      1080
tacatcgata tcggtaagaa agaaggcgcc aagatcttaa ctggtggcga aaaagttggt      1140
gacaagggtt acttcatcag accaaccgtt ttctacgatg ttaatgaaga catgagaatt      1200
gttaaggaag aaattttggg accagttgtc actgtcgcaa agttcaagac tttagaagaa      1260
ggtgtcgaaa tggctaacag ctctgaattc ggtctaggtt ctggtatcga aacagaatct      1320
ttgagcacag gtttgaaggt ggccaagatg ttgaaggccg gtaccgtctg gatcaacaca      1380
tacaacgatt ttgactccag agttccattc ggtggtgtta agcaatctgg ttacggtaga      1440
gaaatgggtg aagaagtcta ccatgcatac actgaagtaa aagctgtcag aattaagttg      1500
tga                                                                   1503

<210> SEQ ID NO 8
<211> LENGTH: 1692
<212> TYPE: DNA
<213> ORGANISM: Saccharomyces cerevisiae
<220> FEATURE:
<221> NAME/KEY: source
<222> LOCATION: 1..1692
<223> OTHER INFORMATION: /mol_type="unassigned DNA"
     /organism="Saccharomyces cerevisiae"

<400> SEQUENCE: 8
atgtctgaaa ttactttggg taaatatttg ttcgaaagat taaagcaagt caacgttaac       60
accgttttcg gtttgccagg tgacttcaac ttgtccttgt tggacaagat ctacgaagtt      120
gaaggtatga gatgggctgg taacgccaac gaattgaacg ctgcttacgc cgctgatggt      180
tacgctcgta tcaagggtat gtcttgtatc atcaccacct tcggtgtcgg tgaattgtct      240
gctttgaacg gtattgccgg ttcttacgct gaacacgtcg gtgttttgca cgttgttggt      300
gtcccatcca tctctgctca agctaagcaa ttgttgttgc accacacctt gggtaacggt      360
gacttcactg ttttccacag aatgtctgcc aacatttctg aaaccactgc tatgatcact      420
gacattgcta ccgccccagc tgaaattgac agatgtatca gaaccactta cgtcacccaa      480
agaccagtct acttaggttt gccagctaac ttggtcgact tgaacgtccc agctaagttg      540
ttgcaaactc caattgacat gtctttgaag ccaaacgatg ctgaatccga aaaggaagtc      600
attgacacca tcttggcttt ggtcaaggat gctaagaacc cagttatctt ggctgatgct      660
```

```
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat tgggtaactt cttgcaagaa   1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta   1320 ttcattggtg acggttcttt gcaattgact gttcaagaaa tctccaccat gatcagatgg   1380
ggcttgaagc catacttgtt cgtcttgaac aacgatggtt acaccattga aaagttgatt   1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga atcatgttg   1620 ccagtcttcg atgctccaca aaacttggtt gaacaagcta gttgactgc tgctaccaac   1680 gctaagcaat ga                                                      1692
```

<210> SEQ ID NO 9
<211> LENGTH: 6702
<212> TYPE: DNA
<213> ORGANISM: Saccharomyces cerevisiae
<220> FEATURE:
<221> NAME/KEY: source
<222> LOCATION: 1..6702
<223> OTHER INFORMATION: /mol_type="unassigned DNA"
    /organism="Saccharomyces cerevisiae"

<400> SEQUENCE: 9

```
atgagcgaag aaagcttatt cgagtcttct ccacagaaga tggagtacga aattacaaac     60
tactcagaaa gacatacaga acttccaggt catttcattg gcctcaatac agtagataaa    120
ctagaggagt ccccgttaag ggactttgtt aagagtcacg gtggtcacac ggtcatatcc    180
aagatcctga tagcaaataa tggtattgcc gccgtgaaag aaattagatc cgtcagaaaa    240
tgggcatacg agacgttcgg cgatgacaga accgtccaat tcgtcgccat ggccacccca    300
gaagatctgg aggccaacgc agaatatatc cgtatggccg atcaatacat tgaagtgcca    360
ggtggtacta ataataacaa ctacgctaac gtagacttga tcgtagacat cgccgaaaga    420
gcagacgtag acgccgtatg ggctggctgg ggtcacgcct ccgagaatcc actattgcct    480
gaaaaattgt cccagtctaa gaggaaagtc atctttattg ggcctccagg taacgccatg    540
aggtctttag gtgataaaat ctcctctacc attgtcgctc aaagtgctaa agtcccatgt    600
attccatggt ctggtacccg tgttgacacc gttcacgtgg acgagaaaac cggtctggtc    660
tctgtcgacg atgacatcta tcaaaagggt tgttgtacct ctcctgaaga tggtttacaa    720
aaggccaagc gtattggttt tcctgtcatg attaaggcat ccgaaggtgg tggtggtaaa    780
ggtatcagac aagttgaacg tgaagaagat ttcatcgctt tataccacca ggcagccaac    840
gaaattccag gctcccccat tttcatcatg aagttggccg gtagagcgcg tcacttggaa    900
```

```
gttcaactgc tagcagatca gtacggtaca aatatttcct tgttcggtag agactgttcc    960
gttcagagac gtcatcaaaa aattatcgaa gaagcaccag ttacaattgc caaggctgaa   1020
acatttcacg agatggaaaa ggctgccgtc agactgggga aactagtcgg ttatgtctct   1080
gccggtaccg tggagtatct atattctcat gatgatggaa aattctactt tttagaattg   1140
aacccaagat tacaagtcga gcatccaaca acggaaatgg tctccggtgt taacttacct   1200
gcagctcaat tacaaatcgc tatgggtatc cctatgcata gaataagtga cattagaact   1260
ttatatggta tgaatcctca ttctgcctca gaaatcgatt tcgaattcaa aactcaagat   1320
gccaccaaga aacaaagaag acctattcca aagggtcatt gtaccgcttg tcgtatcaca   1380
tcagaagatc caaacgatgg attcaagcca tcgggtggta ctttgcatga actaaacttc   1440
cgttcttcct ctaatgtttg gggttacttc tccgtgggta caatggtaa tattcactcc    1500
tttcggact ctcagttcgg ccatattttt gcttttggtg aaaatagaca agcttccagg     1560
aaacacatgg ttgttgccct gaaggaattg tccattaggg gtgatttcag aactactgtg   1620
gaatacttga tcaaactttt ggaaactgaa gatttcgagg ataacactat taccaccggt   1680
tggttggacg atttgattac tcataaaatg accgctgaaa agcctgatcc aactcttgcc   1740
gtcatttgcg gtgccgctac aaaggctttc ttagcatctg aagaagcccg ccacaagtat   1800
atcgaatcct acaaaaggg acaagttcta tctaaagacc tactgcaaac tatgttccct    1860
gtagatttta tccatgaggg taaaagatac aagttcaccg tagctaaatc cggtaatgac   1920
cgttacacat tatttatcaa tggttctaaa tgtgatatca tactgcgtca actagctgat   1980
ggtggtcttt tgattgccat aggcggtaaa tcgcatacca tctattggaa agaagaagtt   2040
gctgctacaa gattatccgt tgactctatg actactttgt tggaagttga aaacgatcca   2100
acccagttgc gtactccatc ccctggtaaa ttggttaaat tcttggtgga aaatggtgaa   2160
cacattatca agggccaacc atatgcagaa attgaagtta tgaaaatgca aatgcctttg   2220
gtttctcaag aaaatggtat cgtccagtta ttaaagcaac ctggttctac cattgttgca   2280
ggtgatatca tggctattat gactcttgac gatccatcca aggtcaagca cgctctacca   2340
tttgaaggta tgctgccaga ttttggttct ccagttatcg aaggaaccaa acctgcctat   2400
aaattcaagt cattagtgtc tactttggaa aacattttga agggttatga caaccaagtt   2460
attatgaacg cttccttgca acaattgata gaggttttga gaaatccaaa actgccttac   2520
tcagaatgga aactacacat ctctgcttta cattcaagat tgcctgctaa gctagatgaa   2580
caaatggaag agttagttgc acgttctttg agacgtggtg ctgttttccc agctagacaa   2640
ttaagtaaat tgattgatat ggccgtgaag aatcctgaat acaaccccga caaattgctg   2700
ggcgccgtcg tggaaccatt ggcggatatt gctcataagt actctaacgg ttagaagcc    2760
catgaacatt ctatatttgt ccatttcttg gaagaatatt acgaagttga aagttattc    2820
aatggtccaa atgttcgtga ggaaaatatc attctgaaat tgcgtgatga aaaccctaaa   2880
gatctagata aagttgcgct aactgttttg tctcattcga aagtttcagc gaagaataac   2940
ctgatcctag ctatcttgaa acattatcaa ccattgtgca agttatcttc taaagtttct   3000
gccatttct ctactcctct acaacatatt gttgaactag aatctaaggc taccgctaag    3060
gtcgctctac aagcaagaga aattttgatt caaggcgctt taccttcggt caaggaaaga   3120
actgaacaaa ttgaacatat cttaaaatcc tctgttgtga aggttgccta tggctcatcc   3180
aatccaaagc gctctgaacc agatttgaat atcttgaagg acttgatcga ttctaattac   3240
gttgtgttcg atgtttttact tcaattccta acccatcaag acccagttgt gactgctgca   3300
```

```
gctgctcaag tctatattcg tcgtgcttat cgtgcttaca ccataggaga tattagagtt   3360
cacgaaggtg tcacagttcc aattgttgaa tggaaattcc aactaccttc agctgcgttc   3420
tccacctttc caactgttaa atctaaaatg ggtatgaaca gggctgttgc tgtttcagat   3480
ttgtcatatg ttgcaaacag tcagtcatct ccgttaagag aaggtatttt gatggctgtg   3540
gatcatttag atgatgttga tgaaattttg tcacaaagtt tggaagttat tcctcgtcac   3600
caatcttctt ctaacggacc tgctcctgat cgttctggta gctccgcatc gttgagtaat   3660
gttgctaatg tttgtgttgc ttctacagaa ggtttcgaat ctgaagagga aattttggta   3720
aggttgagag aaattttgga tttgaataag caggaattaa tcaatgcttc tatccgtcgt   3780
atcacattta tgttcggttt taaagatggg tcttatccaa agtattatac ttttaacggt   3840
ccaaattata acgaaaatga aacaattcgt cacattgagc cggctttggc cttccaactg   3900
gaattaggaa gattgtccaa cttcaacatt aaaccaattt tcactgataa tagaaacatc   3960
catgtctacg aagctgttag taagacttct ccattggata agagattctt tacaagaggt   4020
attattagaa cgggtcatat ccgtgatgac atttctattc aagaatatct gacttctgaa   4080
gctaacagat tgatgagtga tatattggat aatttagaag tcaccgacac ttcaaattct   4140
gatttgaatc atatcttcat caacttcatt gcggtgtttg atatctctcc agaagatgtc   4200
gaagccgcct tcggtggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
aagaacgcaa aaggtgaatg ggtatttaag tctttgggta aacctggatc catgcattta   4440
agacctattg ctactcctta ccctgttaag gaatggttgc aaccaaaacg ttataaggca   4500
cacttgatgg gtaccacata tgtctatgac ttcccagaat tattccgcca agcatcgtca   4560
tcccaatgga aaaatttctc tgcagatgtt aagttaacag atgatttctt tatttccaac   4620
gagttgattg aagatgaaaa cggcgaatta actgaggtgg aaagagaacc tggtgccaac   4680
gctattggta tggttgcctt taagattact gtaaagactc ctgaatatcc aagaggccgt   4740
caatttgttg ttgttgctaa cgatatcaca ttcaagatcg gttcctttgg tccacaagaa   4800
gacgaattct tcaataaggt tactgaatat gctagaaagc gtggtatccc aagaatttac   4860
ttggctgcaa actcaggtgc cagaattggt atggctgaag agattgttcc actatttcaa   4920
gttgcatgga atgatgctgc caatccggac aagggcttcc aatacttata cttaacaagt   4980
gaaggtatgg aaactttaaa gaaatttgac aaagaaaatt ctgttctcac tgaacgtact   5040
gttataaacg gtgaagaaag atttgtcatc aagacaatta ttggttctga agatgggtta   5100
ggtgtcgaat gtctacgtgg atctggttta attgctggtg caacgtcaag ggcttaccac   5160
gatatcttca ctatcaccct agtcacttgt agatccgtcg gtatcggtgc ttatttggtt   5220
cgtttgggtc aaagagctat tcaggtcgaa ggccagccaa ttattttaac tggtgctcct   5280
gcaatcaaca aaatgctggg tagagaagtt tatacttcta acttacaatt gggtggtact   5340
caaatcatgt ataacaacgg tgtttcacat ttgactgctg ttgacgattt agctggtgta   5400
gagaagattg ttgaatggat gtcttatgtt ccagccaagc gtaatatgcc agttcctatc   5460
ttggaaacta agacacatg ggatagacca gttgatttca ctccaactaa tgatgaaact   5520
tacgatgtaa gatggatgat tgaaggtcgt gagactgaaa gtggatttga atatggtttg   5580
tttgataaag ggtctttctt tgaaactttg tcaggatggg ccaaaggtgt tgtcgttggt   5640
```

```
agagcccgtc ttggtggtat tccactgggt gttattggtg ttgaaacaag aactgtcgag    5700
aacttgattc ctgctgatcc agctaatcca aatagtgctg aaacattaat tcaagaacct    5760
ggtcaagttt ggcatccaaa ctccgccttc aagactgctc aagctatcaa tgactttaac    5820
aacggtgaac aattgccaat gatgattttg gccaactgga gaggtttctc tggtggtcaa    5880
cgtgatatgt tcaacgaagt cttgaagtat ggttcgttta ttgttgacgc attggtggat    5940
tacaaacaac caattattat ctatatccca cctaccggtg aactaagagg tggttcatgg    6000
gttgttgtcg atccaactat caacgctgac caaatggaaa tgtatgccga cgtcaacgct    6060
agagctggtg ttttggaacc acaaggtatg gttggtatca agttccgtag agaaaaattg    6120
ctggacacca tgaacagatt ggatgacaag tacagagaat tgagatctca attatccaac    6180
aagagtttgg ctccagaagt catcagcaa atatccaagc aattagctga tcgtgagaga    6240
gaactattgc caatttacgg acaaatcagt cttcaatttg ctgatttgca cgataggtct    6300
tcacgtatgg tggccaaggg tgttatttct aaggaactgg aatggaccga ggcacgtcgt    6360
ttcttcttct ggagattgag aagaagattg aacgaagaat atttgattaa aaggttgagc    6420
catcaggtag gcgaagcatc aagattagaa aagatcgcaa gaattagatc gtggtaccct    6480
gcttcagtgg accatgaaga tgataggcaa gtcgcaacat ggattgaaga aaactacaaa    6540
actttggacg ataaactaaa gggttttgaaa ttagagtcat tcgctcaaga cttagctaaa    6600
aagatcagaa gcgaccatga caatgctatt gatggattat ctgaagttat caagatgtta    6660
tctaccgatg ataaagaaaa attgttgaag actttgaaat ga                      6702
```

<210> SEQ ID NO 10
<211> LENGTH: 3663
<212> TYPE: DNA
<213> ORGANISM: Chloroflexus aurantiacus
<220> FEATURE:
<221> NAME/KEY: source
<222> LOCATION: 1..3663
<223> OTHER INFORMATION: /mol_type="unassigned DNA"
      /organism="Chloroflexus aurantiacus"

<400> SEQUENCE: 10

```
atgagtggta caggtagatt agcaggtaaa atagcattga taacaggtgg tgccggtaac     60
ataggttccg aattaacaag aagatttttg gcagaaggtg ccaccgttat tatctctggt    120
agaaacagag caaagttaac tgccttggct gaaagaatgc aagcagaagc cggtgtccct    180
gctaagagaa ttgatttgga agttatggat ggttctgacc cagtcgctgt aagagcaggt    240
attgaagcca tagtagctag acatggtcaa atcgatatct tggttaacaa cgcaggttca    300
gctggtgcac aaagaagatt ggctgaaatt cctttaactg aagcagaatt gggtccaggt    360
gccgaagaaa cattacatgc atccattgcc aatttgttgg gtatgggttg gcatttgatg    420
agaatagctg caccacacat gcctgttggt agtgcagtta taacgtctc caccatcttc    480 agtagagctg aatattacgg tagaattcct tatgttactc aaaagccgc tttaaatgca    540 ttgtctcaat tagcagccag agaattaggt gctagaggta ttagagttaa caccatattt    600
ccaggtccta tcgaatcaga tagaattaga actgtcttcc aaagaatgga tcaattaaag    660
ggtagacctg aaggtgacac agctcatcac ttttttaaaca ccatgagatt gtgtagagca    720
aacgatcaag gtgccttgga agaagatttt ccatctgtag gtgacgttgc tgacgctgca    780
gtcttcttag cctccgctga agtgccgct ttgtcaggtg aaactattga agttacacat    840
ggtatggaat tgccagcctg ctctgaaaca tcattgttag caagaaccga tttgagaact    900
```

-continued

```
attgacgctt ctggtagaac tacattgatc tgtgctggtg accaaattga agaagtcatg   960
gctttgacag gcatgttaag aacctgcggt tctgaagtaa tcattggttt tagatcagca  1020
gccgctttag ctcaattcga acaagcagtt aatgaatcaa gaagattggc aggtgccgat  1080
tttacaccac ctatagcttt accattagat ccaagagatc cagcaaccat cgatgccgta  1140
ttcgactggg gtgctggtga aaatacaggt ggtatacatg cagccgttat cttaccagct  1200
acctctcacg aaccagcacc ttgtgtcata gaagtagatg acgaaagagt tttgaacttc  1260
ttagctgatg aaatcacagg taccattgtc atagcttcca gattagcaag atattggcaa  1320
agtcaaagat tgactcctgg tgctagagca agaggtccaa gagtaatctt tttgtctaat  1380
ggtgctgatc aaaacggtaa cgtttacggt agaattcaat cagctgcaat aggtcaatta  1440
atcagagttt ggagacatga agctgaattg gattaccaaa gagcatctgc cgctggtgac  1500
cacgtcttac cacctgtatg ggccaatcaa attgttagat ttgctaacag atccttggaa  1560
ggtttagaat cgcctgtgc ttggactgct caattgttgc atagtcaaag acacatcaac  1620
gaaatcacat tgaacatacc agccaacatc tccgctacca ctggtgctag atctgcatca  1680
gttggttggg ctgaaagttt gatcggtttg catttgggta aagtcgcatt gatcacaggt  1740
ggttccgccg gtatcggtgg tcaaattggt agattgttag cattaagtgg tgccagagtt  1800
atgttggcag ccagagatag acataagtta gaacaaatgc aagctatgat tcaatcagaa  1860
ttggcagaag ttggttacac tgatgttgaa gacagagtcc acatagctcc aggttgcgat  1920
gtctcttcag aagcccaatt ggctgactta gtagaaagaa cttttgtctgc tttcggtaca  1980
gttgattatt tgattaataa cgcaggtata gccggtgtag aagaaatggt tatagatatg  2040
cctgttgaag gttggagaca tacattgttc gcaaatttga tctccaacta cagtttgatg  2100
agaaagttgg ctccattaat gaaaaagcaa ggttccggtt acatattgaa cgtttccagt  2160
tacttcggtg gtgaaaaaga tgctgcaata ccatatccta acagagctga ctacgcagtc  2220
tctaaggcag gtcaaagagc aatggccgaa gtatttgcta gattcttagg tcctgaaatc  2280
caaattaatg ctattgcacc aggtcctgtt gaaggtgaca gattaagagg tactggtgaa  2340
agaccaggtt tgtttgccag aagagctaga ttgatcttgg aaaataagag attgaacgaa  2400
ttacatgccg ctttgattgc agccgctaga acagatgaaa gatctatgca cgaattagta  2460
gaattgttgt tgcctaatga cgttgcagcc ttggaacaaa accctgctgc accaactgcc  2520
ttgagagaat tagctagaag attcagatct gaaggtgacc cagccgcttc ttcatccagt  2580
gcattgttga acagatcaat agcagccaag ttattggcta gattacataa cggtggttat  2640
gttttgcctg ctgatatttt tgcaaatttg cctaacccac ctgacccatt tttcacaaga  2700
gcccaaattg atagagaagc tagaaaggtt agagacggta tcatgggcat gttgtacttg  2760
caaagaatgc aaccgaatt tgatgttgcc atggctactg tctattactt agctgacaga  2820
aatgtttccg gtgaaacttt tcatcctagt ggtggttga gatatgaaag aactccaaca  2880
ggtggtgaat tgttcggttt accatctcct gaaagattgg ctgaattagt cggttcaaca  2940
gtatacttaa taggtgaaca tttgaccgaa cacttaaatt tgttggcaag agcctatttg  3000
gaaagatacg gtgcaagaca agttgtcatg attgttgaaa ccgaaactgg tgctgaaaca  3060
atgagaagat tattgcatga tcacgttgaa gctggtagat tgatgaccat tgttgctggt  3120
gaccaaatag aagctgcaat cgaccaagct attactagat atggtagacc aggtcctgta  3180
gtttgtactc cttttagacc attacctaca gttccattgg tcgtagaaa agattctgac  3240
tggtcaacag ttttatcaga agcagaattt gccgaattat gcgaacatca attgactcat  3300
```

```
cacttcagag tcgccagaaa gattgctttg tctgatggtg cttcattagc attggtaacc    3360
ccagaaacaa ccgctacttc cactacgaaa caattcgctt tggcaaactt catcaagacc    3420
actttgcatg ccttcacagc taccattggt gtagaaagtg aaagaactgc tcaaagaata    3480
ttaatcaacc aagttgattt gacaagaaga gccagagctg aagaacctag agacccacac    3540
gaaagacaac aagaattaga aagattcatt gaagcagtat tgttggttac tgccccattg    3600
ccaccagaag cagacacaag atacgcaggt agaatccaca gaggtagagc cattacagtc    3660
tga                                                                  3663
```

<210> SEQ ID NO 11
<211> LENGTH: 2037
<212> TYPE: DNA
<213> ORGANISM: Saccharomyces cerevisiae
<220> FEATURE:
<221> NAME/KEY: source
<222> LOCATION: 1..2037
<223> OTHER INFORMATION: /mol_type="unassigned DNA"
      /organism="Saccharomyces cerevisiae"

<400> SEQUENCE: 11

```
atgggactct tagctttggg cacgcctttg cagtggtttg agtctaggac gtacaatgaa     60
cacataaggg atgaaggtat cgagcagttg ttgtatattt ccaagctgc tggtaaaaga     120 gacaatgacc ctcttttttg gggagacgag cttgagtaca tggttgtaga ttttgatgat    180
aaggagagaa attctatgct cgacgtttgc catgacaaga tactcactga gcttaatatg    240
gaggattcgt cccttgtgag gctaacgat gtgagttttc accctgagta tggccggtat     300
atgttagagg caacaccagc ttctccatat ttgaattacg tgggtagtta cgttgaggtt    360
aacatgcaaa aaagacgtgc cattgcgaaa tataagctat ctgaatatgc gagacaagat    420
agtaaaaata acttgcatgt gggctccagg tctgtccctt tgacgctgac tgtcttcccg    480
aggatgggat gccccgactt tattaacatt aaggatccgt ggaatcataa aaatgccgct    540
tccaggtctc tgtttttacc cgatgaagtc attaacagac atgtcaggtt tcctaacttg    600
acagcatcca tcaggaccag gcgtggtgaa aaagtttgca tgaatgttcc catgtataaa    660
gatatagcta ctccagaaac ggatgactcc atctacgatc gagattggtt tttaccagaa    720
gacaaagagg cgaaactggc ttccaaaccg ggtttcattt atatggattc catgggtttt    780
ggcatgggct gttcgtgctt acaagtgacc tttcaggcac ccaatatcaa caaggcacgt    840
tacctgtacg atgcattagt gaattttgca cctataatgc tagccttctc tgccgctgcg    900
cctgctttta aaggttggct agccgaccaa gatgttcgtt ggaatgtgat atctggtgcg    960
gtggacgacc gtactccgaa ggaaagaggt gttgcgccat tactacccaa atacaacaag    1020
aacggatttg gaggcattgc caaagacgta caagataaag tccttgaaat accaaagtca    1080
agatatagtt cggttgatct tttcttgggt gggtcgaaat ttttcaatag gacttataac    1140
gacacaaatg tacctattaa tgaaaaagta ttaggacgac tactagagaa tgataaggcg    1200
ccactggact atgatcttgc taaacatttt gcgcatctct acataagaga tccagtatct    1260
acattcgaag aactgttgaa tcaggacaac aaaacgtctt caaatcactt tgaaaacatc    1320
caaagtacaa attggcagac attacgtttt aaacccccca cacaacaagc aaccccggac    1380
aaaaaggatt ctcctggttg gagagtggaa ttcagaccat tgaagtgca actattagat     1440 tttgagaacg ctgcgtattc cgtgctcata tacttgattg tcgatagcat tttgaccttt    1500
tccgataata ttaacgcata tattcatatg tccaaagtat gggaaaatat gaagatagcc    1560
```

```
catcacagag atgctatcct atttgaaaaa tttcattgga aaaaatcatt tcgcaacgac    1620
accgatgtgg aaactgaaga ttattctata agcgagattt tccataatcc agagaatggt    1680
atatttcctc aatttgttac gccaatccta tgccaaaaag ggtttgtaac caaagattgg    1740
aaagaattaa agcattcttc caaacacgag agactatact attatttaaa gctaatttct    1800
gatagagcaa gcggtgaatt gccaacaaca gcaaaattct ttagaaattt tgtactacaa    1860
catccagatt acaaacatga ttcaaaaatt tcaaagtcga tcaattatga tttgctttct    1920
acgtgtgata gacttaccca tttagacgat tcaaaaggtg aattgacatc cttttttagga   1980 gctgaaattg cagaatatgt aaaaaaaaat aagccttcaa tagaaagcaa atgttaa       2037

<210> SEQ ID NO 12
<211> LENGTH: 1476
<212> TYPE: DNA
<213> ORGANISM: Saccharomyces cerevisiae
<220> FEATURE:
<221> NAME/KEY: source
<222> LOCATION: 1..1476
<223> OTHER INFORMATION: /mol_type="unassigned DNA"
      /organism="Saccharomyces cerevisiae"

<400> SEQUENCE: 12
atggcacact atccaccttc caaggatcaa ttgaatgaat tgatccagga agttaaccaa      60
tgggctatca ctaatggatt atccatgtat cctcctaaat tcgaggagaa cccatcaaat     120
gcatcggtgt caccagtaac tatctatcca accccaattc ctaggaaatg ttttgatgag     180
gccgttcaaa tacaaccggt attcaatgaa ttatacgccc gtattaccca agatatggcc     240
caacctgatt cttatttaca taaaacaact gaagcgttag ctctatcaga ttccgagttt     300
actggaaaac tgtggtctct ataccttgct accttaaaat ctgcacagta caaaaagcag     360
aattttaggc taggtatatt tagatcagat tatttgattg ataagaaaaa gggtactgaa     420
cagattaagc aagtcgagtt taatacagtg tcagtgtcat ttgcaggcct tagcgagaaa     480
gttgatagat tgcactctta tttaaatagg gcaaacaagt acgatcctaa aggaccaatt     540
tataatgatc aaaaatatggt catttctgat tcaggatacc ttttgtctaa ggcattggcc     600
aaagctgtgg aatcgtataa gtcacaacaa agttcttcta caactagtga tcctattgtc     660
gcattcattg tgcaaagaaa cgagagaaat gtgtttgatc aaaaggtctt ggaattgaat     720
ctgttggaaa aattcggtac caaatctgtt aggttgacgt ttgatgatgt taacgataaa     780
ttgttcattg atgataaaac gggaaagctt tcattaggg acacagagca ggaaatagcg     840
gtggtttatt acagaacggg ttacacaacc actgattaca cgtccgaaaa ggactgggag     900
gcaagactat tcctcgaaaa aagtttcgca ataaaggccc cagatttact cactcaatta     960
tctggctcca agaaaattca gcaattgttg acagatgagg gcgtattagg taaatacatc    1020
tccgatgctg agaaaagag tagtttgtta aaaactttg tcaaaatata tcccttggat    1080
gatacgaagc ttggcaggga aggcaagagg ctggcattaa gtgagccctc taaatacgtg   1140
ttaaaaccac agcgggaagg tggcggaaac aatgtttata agaaaatat tcctaatttt    1200 ttgaaaggta tcgaagaacg tcactgggat gcatatattc tcatggagtt gattgaacca    1260
gagttgaatg aaaataatat tatattacgt gataacaaat cttacaacga accaatcatc    1320
agtgaactag gaatttatgg ttgcgttcta tttaacgacg agcaagtttt atcgaacgaa    1380
tttagtggct cattactaag atccaaattt aatacttcaa atgaaggtgg agtggcggca    1440
ggattcggat gtttggacag tattattctt tactag                              1476
```

<210> SEQ ID NO 13
<211> LENGTH: 1404
<212> TYPE: DNA
<213> ORGANISM: Saccharomyces cerevisiae
<220> FEATURE:
<221> NAME/KEY: source
<222> LOCATION: 1..1404
<223> OTHER INFORMATION: /mol_type="unassigned DNA"
      /organism="Saccharomyces cerevisiae"

<400> SEQUENCE: 13

| | | | | | |
|---|---|---|---|---|---|
| ttgtaattaa | aacttagatt | agattgctat | gctttctttc | taatgagcaa | gaagtaaaaa | 60 |
| aagttgtaat | agaacaagaa | aaatgaaact | gaaacttgag | aaattgaaga | ccgtttatta | 120 |
| acttaaatat | caatgggagg | tcatcgaaag | agaaaaaaat | caaaaaaaaa | aattttcaag | 180 |
| aaaagaaac | gtgataaaaa | ttttattgc | cttttcgac | gaagaaaaag | aaacgaggcg | 240 |
| gtctcttttt | tcttttccaa | acctttagta | cgggtaatta | acgacaccct | agaggaagaa | 300 |
| agagggaaa | tttagtatgc | tgtgcttggg | tgttttgaag | tggtacggcg | atgcgcggag | 360 |
| tccgagaaaa | tctggaagag | taaaaaagga | gtagaaacat | tttgaagcta | tggtgtgtgc | 420 |
| ggaagtacct | tcaaagaatg | gggtcttatc | ttgttttgca | agtaccactg | agcaggataa | 480 |
| taatagaaat | gataatatac | tatagtagag | ataacgtcga | tgacttccca | tactgtaatt | 540 |
| gcttttagtt | gtgtattttt | agtgtgcaag | tttctgtaaa | tcgattaatt | ttttttttctt | 600 |
| tcctctttt | attaaccta | attttattt | tagattcctg | acttcaactc | aagacgcaca | 660 |
| gatattataa | catctgcata | ataggcattt | gcaagaatta | ctcgtgagta | aggaaagagt | 720 |
| gaggaactat | cgcatacctg | catttaaaga | tgccgatttg | ggcgcgaatc | ctttattttg | 780 |
| gcttcaccct | catactatta | tcagggccag | aaaaaggaag | tgtttccctc | cttcttgaat | 840 |
| tgatgttacc | ctcataaagc | acgtggcctc | ttatcgagaa | agaaattacc | gtcgctcgtg | 900 |
| atttgtttgc | aaaaagaaca | aaactgaaaa | aacccagaca | cgctcgactt | cctgtcttcc | 960 |
| tattgattgc | agcttccaat | ttcgtcacac | aacaaggtcc | tagcgacggc | tcacaggttt | 1020 |
| tgtaacaagc | aatcgaaggt | tctggaatgg | cgggaaaggg | tttagtacca | catgctatga | 1080 |
| tgcccactgt | gatctccaga | gcaaagttcg | ttcgatcgta | ctgttactct | ctctctttca | 1140 |
| aacagaattg | tccgaatcgt | gtgacaacaa | cagcctgttc | tcacacactc | ttttcttcta | 1200 |
| accaaggggg | tggtttagtt | tagtagaacc | tcgtgaaact | tacatttaca | tatatataaa | 1260 |
| cttgcataaa | ttggtcaatg | caagaaatac | atatttggtc | ttttctaatt | cgtagttttt | 1320 |
| caagttctta | gatgctttct | ttttctcttt | tttacagatc | atcaaggaag | taattatcta | 1380 |
| cttttttacaa | caaatataaa | acaa | | | | 1404 |

<210> SEQ ID NO 14
<211> LENGTH: 609
<212> TYPE: DNA
<213> ORGANISM: Saccharomyces cerevisiae
<220> FEATURE:
<221> NAME/KEY: source
<222> LOCATION: 1..609
<223> OTHER INFORMATION: /mol_type="unassigned DNA"
      /organism="Saccharomyces cerevisiae"

<400> SEQUENCE: 14

| | | | | | |
|---|---|---|---|---|---|
| atggctacta | atattacttg | gcatccaaat | cttacttacg | acgaacgcaa | ggcattgaga | 60 |
| aaacaggacg | gttgtactat | ttggttaaca | ggtctaagtg | cgtcaggtaa | aagtacaatc | 120 |

```
gcctgtgcgc tagaacagtt actgctccaa aaaaacttgt ctgcatatag attggatggt      180
gacaacattc gttttggatt gaacaaggat ttgggtttct cagaaaagga cagaaatgaa      240
aacattcgta gaattagcga agtttctaag ctatttgctg attcatgtgc tatttcaatc      300
acctcattta tctctccata cagagttgac agagatagag ctcgtgaact acataaggag      360
gctggtttga agttcattga aatatttgtt gatgttccat tagaagtcgc tgagcaaagg      420
gaccctaagg gttatacaa gaaagctagg gagggtgtaa tcaaggagtt tacaggtatt       480
tctgccccat atgaagcgcc aaaagctcca gagctacatt tgagaaccga ccagaagacg      540
gttgaagaat gtgctaccat tatttatgag tacttaatca gtgaaaaaat catccgtaag      600
catttgtaa                                                              609
```

<210> SEQ ID NO 15
<211> LENGTH: 786
<212> TYPE: DNA
<213> ORGANISM: Saccharomyces cerevisiae
<220> FEATURE:
<221> NAME/KEY: source
<222> LOCATION: 1..786
<223> OTHER INFORMATION: /mol_type="unassigned DNA"
       /organism="Saccharomyces cerevisiae"

<400> SEQUENCE: 15

```
atgaagacct atcatttgaa taatgatata attgtcacac aagaacagtt ggatcattgg       60
aatgaacaac taatcaagct ggaaacgcca caggagatta ttgcatggtc tatcgtaacg      120
tttcctcacc ttttccaaac cactgcattt ggtttgactg gcttggttac tatcgatatg      180
ttgtcaaagc tatctgaaaa atactacatg ccagaactat tatttataga cactttgcac      240
catttcccac aaactttaac actaaaaaac gagattgaga aaaatactac ccagcctaaa      300
aatcaaacca ttcacgtata taagccggat ggatgtgaat cggaggcaga ttttgcctcg      360
aaatacgggg atttcttatg ggagaaagat gatgacaagt acgattatct ggccaaagtg      420
gaacctgcac atcgtgccta caaagagcta catataagtg ctgtgtttac tggtagaaga      480
aaatcacaag ttctgcccg ctcccaactg tcgattattg aaatagacga acttaatgga       540
atcttaaaaa taaatccatt gatcaattgg acgttcgagc aggttaaaca gtatatagat      600
gcaaacaatg taccatacaa cgaactttg gaccttggat atagatccat tggtgattac       660
cattccacac aacccgtcaa ggaaggtgaa gatgagagag caggaagatg gaagggcaag      720
gccaagaccg agtgtggaat tcatgaagcc agccgattcg cgcaattttt aaagcaagat      780
gcctag                                                                 786
```

<210> SEQ ID NO 16
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
       /note="primer"
       /organism="Artificial Sequence"

<400> SEQUENCE: 16

```
cagaatttgt tggcctattt tctta                                             25
```

<210> SEQ ID NO 17
<211> LENGTH: 25
<212> TYPE: DNA

```
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="primer"
      /organism="Artificial Sequence"

<400> SEQUENCE: 17
caatacgttg gtagttagga acagg                                            25

<210> SEQ ID NO 18
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer"
      /organism="Artificial Sequence"

<400> SEQUENCE: 18
gatgctcatc acagactact                                                  20

<210> SEQ ID NO 19
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="primer"
      /organism="Artificial Sequence"

<400> SEQUENCE: 19
agtgacgact gaatccggtg                                                  20

<210> SEQ ID NO 20
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="primer"
      /organism="Artificial Sequence"

<400> SEQUENCE: 20
acctgcactt tgtaattaaa acttag                                           26

<210> SEQ ID NO 21
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="primer"
      /organism="Artificial Sequence"

<400> SEQUENCE: 21
cacgcgatgc acaccata gcttc                                              25

<210> SEQ ID NO 22
<211> LENGTH: 33
```

```
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="primer"
      /organism="Artificial Sequence"

<400> SEQUENCE: 22
agtgcaggta aaacaatgtc cgccgctact gtt                                    33

<210> SEQ ID NO 23
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="primer"
      /organism="Artificial Sequence"

<400> SEQUENCE: 23
cgtgcgattc attttatttc atcagacttc aaga                                   34

<210> SEQ ID NO 24
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="prmer"
      /organism="Artificial Sequence"

<400> SEQUENCE: 24
agctgttctc tattttattt catcagactt caagacg                                37

<210> SEQ ID NO 25
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="primer"
      /organism="Artificial Sequence"

<400> SEQUENCE: 25
agtggcctga gtacttaatt aaactaagta agcatgactc                             40

<210> SEQ ID NO 26
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="primer"
      /organism="Artificial Sequence"

<400> SEQUENCE: 26
gtctaccgtg atttcttcaa cactt                                             25

<210> SEQ ID NO 27
```

```
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer"
      /organism="Artificial Sequence"

<400> SEQUENCE: 27
tggaagaggc aagcacgtta gc                                              22

<210> SEQ ID NO 28
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer"
      /organism="Artificial Sequence"

<400> SEQUENCE: 28
cagaagcata actacccatt cc                                              22

<210> SEQ ID NO 29
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="primer"
      /organism="Artificial Sequence"

<400> SEQUENCE: 29
agaacagctg aagcttcgta cg                                              22

<210> SEQ ID NO 30
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="primer"
      /organism="Artificial Sequence"

<400> SEQUENCE: 30
aggccactag tggatctgat atcac                                           25

<210> SEQ ID NO 31
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="primer"
      /organism="Artificial Sequence"

<400> SEQUENCE: 31
cacgcgatgc acacaccata gcttc                                           25
```

```
<210> SEQ ID NO 32
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="primer"
      /organism="Artificial Sequence"

<400> SEQUENCE: 32
agtgcaggta aaacaatggg actcttagct ttggg                               35

<210> SEQ ID NO 33
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="primer"
      /organism="Artificial Sequence"

<400> SEQUENCE: 33
cgtgcgattc aacatttgct ttctattgaa ggc                                 33

<210> SEQ ID NO 34
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="primer"
      /organism="Artificial Sequence"

<400> SEQUENCE: 34
atctgtcata aaacaatggc acactatcca ccttcc                              36

<210> SEQ ID NO 35
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="primer"
      /organism="Artificial Sequence"

<400> SEQUENCE: 35
cacgcgattc agtaaagaat aatactgtcc                                     30

<210> SEQ ID NO 36
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="primer"
      /organism="Artificial Sequence"

<400> SEQUENCE: 36
agtgcaggta aaacaatggc tactaatatt acttggc                             37
```

<210> SEQ ID NO 37
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
    /note="primer"
    /organism="Artificial Sequence"

<400> SEQUENCE: 37
cgtgcgattc acaaatgctt acggatgatt ttttc                              35

<210> SEQ ID NO 38
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
    /note="primer"
    /organism="Artificial Sequence"

<400> SEQUENCE: 38
atctgtcata aaacaatgaa gacctatcat ttg                                33

<210> SEQ ID NO 39
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
    /note="primer"
    /organism="Artificial Sequence"

<400> SEQUENCE: 39
cacgcgattc aggcatcttg ctttaaaaat tgc                                33

<210> SEQ ID NO 40
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
    /note="primer"
    /organism="Artificial Sequence"

<400> SEQUENCE: 40
ataccgttgc agtatttggc tccgggactg tag                                33

<210> SEQ ID NO 41
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
    /note="primer"
    /organism="Artificial Sequence"

<400> SEQUENCE: 41
ctacagtccc ggagccaaat actgcaacgg tat                                33

<210> SEQ ID NO 42
<211> LENGTH: 53
<212> TYPE: DNA
<213> ORGANISM: Artificial Sequence
<220> FEATURE:
<221> NAME/KEY: source
<222> LOCATION: 1..53
<223> OTHER INFORMATION: /mol_type="unassigned DNA"
      /note="primer"
      /organism="Artificial Sequence"

<400> SEQUENCE: 42
gccattgaca ttaacaataa gaaaaaacaa tattcttctc aatttggtgc cac           53

<210> SEQ ID NO 43
<211> LENGTH: 53
<212> TYPE: DNA
<213> ORGANISM: Artificial Sequence
<220> FEATURE:
<221> NAME/KEY: source
<222> LOCATION: 1..53
<223> OTHER INFORMATION: /mol_type="unassigned DNA"
      /note="primer"
      /organism="Artificial Sequence"

<400> SEQUENCE: 43
gtggcaccaa attgagaaga atattgtttt ttcttattgt taatgtcaat ggc           53

<210> SEQ ID NO 44
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="primer"
      /organism="Artificial Sequence"

<400> SEQUENCE: 44
gagagatgct ttggaagcct ctcataaagg ttggg                              35

<210> SEQ ID NO 45
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="primer"
      /organism="Artificial Sequence"

<400> SEQUENCE: 45
cccaaccttt atgagaggct tccaaagcat ctctc                              35

<210> SEQ ID NO 46
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="primer"
      /organism="Artificial Sequence"

<400> SEQUENCE: 46

```
ggggtctgga ttttactttt gacggtactg gtaataccaa aattatg         47
```

<210> SEQ ID NO 47
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="primer"
      /organism="Artificial Sequence"

<400> SEQUENCE: 47

```
cataattttg gtattaccag taccgtcaaa agtaaaatcc agacccc         47
```

<210> SEQ ID NO 48
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="primer"
      /organism="Artificial Sequence"

<400> SEQUENCE: 48

```
ggggtctgga ttttactttt gacgctactg gtaataccaa aattatg         47
```

<210> SEQ ID NO 49
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="primer"
      /organism="Artificial Sequence"

<400> SEQUENCE: 49

```
cataattttg gtattaccag tagcgtcaaa agtaaaatcc agacccc         47
```

<210> SEQ ID NO 50
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="primer"
      /organism="Artificial Sequence"

<400> SEQUENCE: 50

```
gggggtctgg attttacttt tgacgttact ggtaatacca aaattatgag      50
```

<210> SEQ ID NO 51
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="primer"
      /organism="Artificial Sequence"

<400> SEQUENCE: 51
ctcataattt tggtattacc agtaacgtca aaagtaaaat ccagaccccc           50

<210> SEQ ID NO 52
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="primer"
      /organism="Artificial Sequence"

<400> SEQUENCE: 52
ggggtctgga ttttactttt gacactactg gtataccaa aattatg              47

<210> SEQ ID NO 53
<211> LENGTH: 47
<212> TYPE: DNA
<213> ORGANISM: Artificial Sequence
<220> FEATURE:
<221> NAME/KEY: source
<222> LOCATION: 1..47
<223> OTHER INFORMATION: /mol_type="unassigned DNA"
      /note="primer"
      /organism="Artificial Sequence"

<400> SEQUENCE: 53
cataattttg gtattaccag tagtgtcaaa agtaaaatcc agacccc             47

<210> SEQ ID NO 54
<211> LENGTH: 45
<212> TYPE: DNA
<213> ORGANISM: Artificial Sequence
<220> FEATURE:
<221> NAME/KEY: source
<222> LOCATION: 1..45
<223> OTHER INFORMATION: /mol_type="unassigned DNA"
      /note="primer"
      /organism="Artificial Sequence"

<400> SEQUENCE: 54
cttttgactg tactggtaat accaaaattg tgagagatgc tttgg              45

<210> SEQ ID NO 55
<211> LENGTH: 45
<212> TYPE: DNA
<213> ORGANISM: Artificial Sequence
<220> FEATURE:
<221> NAME/KEY: source
<222> LOCATION: 1..45
<223> OTHER INFORMATION: /mol_type="unassigned DNA"
      /note="primer"
      /organism="Artificial Sequence"

<400> SEQUENCE: 55
ccaaagcatc tctcacaatt ttggtattac cagtacagtc aaaag              45

<210> SEQ ID NO 56
<211> LENGTH: 51
<212> TYPE: DNA
<213> ORGANISM: Artificial Sequence
<220> FEATURE:
<221> NAME/KEY: source
<222> LOCATION: 1..51
<223> OTHER INFORMATION: /mol_type="unassigned DNA"
      /note="primer"
      /organism="Artificial Sequence"

```
<400> SEQUENCE: 56
ttacttttga ctgtactggt aataccaaaa ttgcgagaga tgctttggaa g          51

<210> SEQ ID NO 57
<211> LENGTH: 51
<212> TYPE: DNA
<213> ORGANISM: Artificial Sequence
<220> FEATURE:
<221> NAME/KEY: source
<222> LOCATION: 1..51
<223> OTHER INFORMATION: /mol_type="unassigned DNA"
      /note="primer"
      /organism="Artificial Sequence"

<400> SEQUENCE: 57
cttccaaagc atctctcgca attttggtat taccagtaca gtcaaaagta a          51
```